US006207368B1

(12) United States Patent
Adams

(10) Patent No.: US 6,207,368 B1
(45) Date of Patent: Mar. 27, 2001

(54) METHODS AND REAGENTS FOR CONTROLLING CHAIN EXTENSION AND LIGATION CHAIN REACTIONS

(75) Inventor: Craig W. Adams, Corona, CA (US)

(73) Assignee: Beckman Coulter, Inc., Fullerton, CA (US)

(*) Notice: Subject to any disclaimer, the term of this patent is extended or adjusted under 35 U.S.C. 154(b) by 0 days.

(21) Appl. No.: 08/361,024

(22) Filed: Dec. 21, 1994

Related U.S. Application Data

(63) Continuation of application No. 07/925,059, filed on Aug. 4, 1992, now abandoned.

(51) Int. Cl.[7] .................................................. C12Q 1/68
(52) U.S. Cl. ................................................. 435/6; 536/24.3
(58) Field of Search ........................ 435/6, 91.2; 935/77, 935/78; 536/24.3, 24.33

(56) References Cited

U.S. PATENT DOCUMENTS

| | | | |
|---|---|---|---|
| 4,683,195 | 7/1987 | Mullis et al. ............................ | 435/6 |
| 4,683,202 | 7/1987 | Mullis et al. ........................... | 435/71 |
| 4,883,750 | 11/1989 | Whiteley et al. ........................ | 435/6 |
| 4,988,617 | 1/1991 | Landegren et al. ...................... | 435/6 |
| 4,994,370 | 2/1991 | Silver et al. . | |
| 5,185,243 | 2/1993 | Ullman et al. ........................... | 434/6 |

FOREIGN PATENT DOCUMENTS

| | | | |
|---|---|---|---|
| 0 258 017 A2 | 3/1988 | (EP) . | |
| 0 292 128 A1 | 11/1988 | (EP) . | |
| 0 327 429 A2 | 1/1989 | (EP) . | |
| 0 332 435 | 9/1989 | (EP) ................................. | C12Q/1/68 |
| 0 373 962 A2 | 12/1989 | (EP) . | |
| 0 357 336 A3 | 3/1990 | (EP) ................................. | C12Q/1/68 |
| 0 439 182 A2 | 7/1991 | (EP) . | |
| 0 450 594 A2 | 10/1991 | (EP) . | |
| 0 451 591 A1 | 10/1991 | (EP) . | |
| 0 473 155 A2 | 3/1992 | (EP) . | |
| 0 477 972 A2 | 4/1992 | (EP) . | |
| 2 225 112A | 5/1990 | (GB) ............................. | G01N/33/53 |
| WO 89/09835 | 10/1989 | (WO) . | |
| WO 89/12696 | 12/1989 | (WO) . | |
| WO 90/01069 | 2/1990 | (WO) . | |
| WO 91/17239 | 11/1991 | (WO) . | |
| WO 91/17270 | 11/1991 | (WO) . | |

OTHER PUBLICATIONS

Wright, Pat A. & Wynford–Thomas, David, The Polymerase Chain Reaction: MIracle or Mirage? A Critical Review of its Uses and Limitations in Diagnosis and Research; Journey of Pathology, vol. 162:99–117 (1990).

(List continued on next page.)

*Primary Examiner*—Scott W. Houtteman
(74) *Attorney, Agent, or Firm*—William H. May; Arnold Grant

(57) ABSTRACT

Disclosed herein are methods for the detection and exponential amplification of a target nucleic acid sequence. In a preferred embodiment, the methodology relies upon three oligonucleotide moieties: a Blocker moiety capable of hybridizing to a target sequence; a Primer moiety capable of hybridizing to the target sequence in an adjacent fashion to the Blocker moiety; and an End-Run moiety having a sequence which is complementary to the Blocker moiety. A ligation event between the hybridized Blocker and Primer moieties, followed by elongation of the End-Run moiety along the ligated Blocker and Primer moieties, provides multiple copies of target sequence such that during cyclical amplification, exponential amounts of the original target sequence are provided.

7 Claims, 11 Drawing Sheets

OTHER PUBLICATIONS

Wu, Dan Y. & Wallace, R. Bruce, "The Ligation Amplification Reaction (LAR)—Amplification of Specific DNA Sequential Rounds of Template–Dependent Ligation"; Genomics 4, 500–569 (1989).

Amplification of Nucleic Acid Sequences: The Choices Multiply, The Journal of NIH Research (Methods and Materials), pp. 81–86; Feb. 1991 (vol. 3); Author Unknown.

Formation of Covalent Circles of Lambda DNA by *E. coli* Extracts, Biochemistry, pp. 148–155:1967 (vol. 57); M. Gellert.

The Enzymatic Repair of DNA,I. Formation of Circular λDNA, Biochemistry, pp. 240–247:Apr. 19, 1967 (vol. 58) Gefter et al.

Enzymatic Breakage and Joining of Deoxyribonucleic Acid, I. Repair of Single–Strand Breaks in DNA by Enzyme System from Escherichia coli infected with T4 Bacteriophage, Biochemistry; pp. 1021–1028:Feb. 13, 1967; Weiss and Richardson.

Linkage of Polynucleotides Through Phosphodiester Bonds By An Enzyme From *Escherichia coli*, Biochemistry (vol. 57) pp. 1426–1433:1967; Olivera and Lehman.

The Ligase Chain Reaction in a PCR World, pp. 5–16:1991; PCR Methods and Applications, F. Barany.

Genetic Disease Detection and DNA Amplification Using Cloned Thermostable Ligase, pp. 189–193:Jan. 1991 (vol. 88); Proc. Natl. Acad. Sci. F. Barany.

Specific Enzymatic Amplification of DNA in Vitro: The Polymerase Chain Reaction pp. 263–273:1986, Cold Spring Harbor Symposia on Quantitative Biology (vol. L1) K. Mullis, F. Faloona, S. Scharf, R. Saiki, G. Horn, and H. Erlich.

Specific Synthesis DNA in Vitro via a Polymerase–Catalyzed Chain Reaction, pp. 335–350:1987 Methods in Enzymology, (vol. 155) K. Mullis, Fred A. Faloona.

Cystic Fibrosis: Molecular Biology and Therapeutic Implications, pp. 774–779:May 8, 1992 Science (vol. 256) Francis S. Collins.

Hot Prospect for New Gene Amplifier, pp. 254–257:Nov. 29, 1992, Science (vol. 254) Rick Weiss.

Triplet Repeat Mutations in Human Disease, pp. 784–789:May 8, 1992, Science (vol. 256) C. Thomas Caskey et al.

Malignant Hyperthermia, pp. 789–794:May 8, 1992, Science (vol. 256) D.H. MacLennan et al.

DNA Ligase: Structure, Mechanism, and Function, pp. 790–797:Nov. 29, 1974, Science (vol. 186) I.R. Lehman.

Gaucher Disease: New Molecular Approaches to Diagnosis and Treatment, pp. 794–799:May 8, 1992 Science (vol. 256); E. Beutler.

Molecular Genetics of *Epidermolysis bullosa*, pp. 799–804:May 8, 1992, Science (vol. 256) E. Epstein, Jr.

On the Molecular Genetics of Reinitis Pigmentos, pp. 804–808:May 8, 1992 Science (vol. 256); P. Humphries et al.

Human Gene Therapy, pp. 808–813:May 8, 1992; Science (vol. 256); W. French Anderson.

A Ligase–Medicated Gene Detection Technique, pp. 1077–1080:Aug. 26, 1988; Science (vol. 241) Landegren, Kaiser, Sanders, Hood.

Sequence–Selective Recognition of DNA by Strand Displacement with a Thymine–Substituted Polyamide, pp. 1497–1500:Dec. 6, 1991; Science (vol. 254); P.E. Nielsen.

Peptide Nucleic Acids (PNA). Oligonucleotide Analogues with an Achiral Peptdie Backbone, pp. 1895–1897:1986; J. Am. Chem. Soc., vol. 114, No. 5; M. Egholm.

Automated DNA Diagnostics Using a ELISA–based Oligonucleotide Ligation Assay, pp. 8923–8927:Jun.16, 1990; Proc. Natl. Acad. Sci., vol. 87, D. Nickerson.

Alzheimer's Disease: A Cell Biological Perspective, pp. 780–783:May 8, 1992; Science (vol. 256); K. Kosik.

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 4 bases
      (B) TYPE: nucleic acid
      (C) STRANDEDNESS: single
      (D) TOPOLOGY: linear (ii) MOLECULE TYPE: DNA (genomic)

(iii) HYPOTHETICAL: yes (iv) ANTI-SENSE: no (xi) SEQUENCE DESCRIPTION: SEQ ID NO:1:

ATCG (2) INFORMATION FOR SEQ ID NO: 2:

(i) SEQUENCE CHARACTERISTICS:
        (A) LENGTH:  4 bases
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  yes (iv) ANTI-SENSE:  no (xi) SEQUENCE DESCRIPTION:  SEQ ID NO:2:

TAGC                                                                           4

(2) INFORMATION FOR SEQ ID NO: 3:

(i) SEQUENCE CHARACTERISTICS:
        (A) LENGTH:  2 bases
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  yes (iv) ANTI-SENSE:  no (xi) SEQUENCE DESCRIPTION:  SEQ ID NO:3:

GC                                                                             2

(2) INFORMATION FOR SEQ ID NO: 4:

(i) SEQUENCE CHARACTERISTICS:
        (A) LENGTH:  4 bases
        (B) TYPE:  nucleic acid
        (C) STRANDEDNESS:  single, including nick
        (D) TOPOLOGY:  linear (ii) MOLECULE TYPE:  DNA (genomic)

(iii) HYPOTHETICAL:  yes (iv) ANTI-SENSE:  no (xi) SEQUENCE DESCRIPTION:  SEQ ID NO:4:

TAGC                                                                           4

(2) INFORMATION FOR SEQ ID NO: 5:

(i) SEQUENCE CHARACTERISTICS:
        (A) LENGTH:  10 bases
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  yes (iv) ANTI-SENSE:  no (xi) SEQUENCE DESCRIPTION:  SEQ ID NO:5:

ACG TTT CCC C                                                             10

(2) INFORMATION FOR SEQ ID NO: 6:

```
        (i) SEQUENCE CHARACTERISTICS:
            (A) LENGTH:  4 bases
            (B) TYPE:  nucleic acid
            (C) STRANDEDNESS:  single
            (D) TOPOLOGY:  linear (ii) MOLECULE TYPE:  DNA (genomic)

(iii) HYPOTHETICAL:  yes (iv) ANTI-SENSE:  no (xi) SEQUENCE DESCRIPTION:  SEQ ID NO:6:

TGCA                                                                     4

(2) INFORMATION FOR SEQ ID NO: 7:

(i) SEQUENCE CHARACTERISTICS:
            (A) LENGTH:  4 bases
            (B) TYPE:  nucleic acid
            (C) STRANDEDNESS:  single
            (D) TOPOLOGY:  linear (ii) MOLECULE TYPE:  DNA (genomic)

(iii) HYPOTHETICAL:  yes (iv) ANTI-SENSE:  no (xi) SEQUENCE DESCRIPTION:  SEQ ID NO:7:

GGGG                                                                     4

(2) INFORMATION FOR SEQ ID NO: 8:

(i) SEQUENCE CHARACTERISTICS:
            (A) LENGTH:  50 bases
            (B) TYPE:  nucleic acid
            (C) STRANDEDNESS:  single
            (D) TOPOLOGY:  linear (ii) MOLECULE TYPE:  DNA (genomic)

(iii) HYPOTHETICAL:  no (iv) ANTI-SENSE:  no (xi) SEQUENCE DESCRIPTION:  SEQ ID NO:8:

GCC CTT CCC AAC AGT TGC GCA GCC                                         24

TGA ATG GCG AAT GGC GCT TTG CCT GG                                      50

(2) INFORMATION FOR SEQ ID NO: 9:

(i) SEQUENCE CHARACTERISTICS:
            (A) LENGTH:  23 bases
            (B) TYPE:  nucleic acid
            (C) STRANDEDNESS:  single
            (D) TOPOLOGY:  linear (ii) MOLECULE TYPE:  DNA (genomic)

(iii) HYPOTHETICAL:  no (iv) ANTI-SENSE:  no (xi) SEQUENCE DESCRIPTION:  SEQ ID NO:9:

CCA TTC AGG CTG CGC AAC TGT TG                                          23

(2) INFORMATION FOR SEQ ID NO: 10:

(i) SEQUENCE CHARACTERISTICS:
```

```
            (A) LENGTH:  10 bases
            (B) TYPE:  nucleic acid
            (C) STRANDEDNESS:  single
            (D) TOPOLOGY:  linear (ii) MOLECULE TYPE:  DNA (genomic)

(iii) HYPOTHETICAL:  no (iv) ANTI-SENSE:  no (xi) SEQUENCE DESCRIPTION:  SEQ ID NO:10:

GCG CCA TTC G                                                        10

(2) INFORMATION FOR SEQ ID NO: 11:

(i) SEQUENCE CHARACTERISTICS:
            (A) LENGTH:  18 bases
            (B) TYPE:  nucleic acid
            (C) STRANDEDNESS:  single
            (D) TOPOLOGY:  linear (ii) MOLECULE TYPE:  DNA (genomic)

(iii) HYPOTHETICAL:  no (iv) ANTI-SENSE:  no (xi) SEQUENCE DESCRIPTION:  SEQ ID NO:11:

GTT GCG CAG CCT GAA TGG                                              18
```

METHODS AND REAGENTS FOR CONTROLLING CHAIN EXTENSION AND LIGATION CHAIN REACTIONS

This is a continuation of application Ser. No. 07/925,059, filed Aug. 4, 1992 now abandoned.

FIELD OF INVENTION

The present invention relates to the analysis of deoxyribonucleic acid ("DNA") and ribonucleic acid ("RNA"), the determination of the presence of specific DNA and/or RNA nucleotide sequences, and the exponential amplification of such sequences.

BACKGROUND OF THE INVENTION

The references to be discussed throughout this document are set forth solely for the information described therein prior to the filing date of this document, and nothing herein is to be construed as an admission, either express or implied, that the references are "prior art" or that the inventor is not entitled to antedate such descriptions by virtue of prior invention or priority based on earlier filed applications.

I. Introduction

The amplification of desired portions or entire sequences of DNA and RNA finds utility in a variety of fields, from criminal investigations (where DNA obtained from crime scene samples are compared with the DNA from an accused individual), to archeology (where the DNA of ancient plants, animals, sub-human species and humans are analyzed), to paternity analysis (where the DNA from the offspring and a possible parent are comparatively analyzed), to genetic analysis (where the DNA of individuals are analyzed for an indication of the possibility of genetic variation which is indicative of a particular disease state). Amplification of the nucleic acid sequence is most typically necessary because whatever DNA may be present from the source is extremely limited such that in order to properly analyze such DNA, many more copies of the original RNA are required.

The ability to amplify nucleic acid sequences is relatively recent (1985), but the impact of this ability has been phenomenal—without such amplification, most of the foregoing exemplary fields would not be possible. Thus, as the areas in which DNA amplification has expanded, the requirements placed upon various amplification techniques have changed. Accordingly, a very real and ongoing need exists for highly specific amplification techniques.

II. The Genetic Code (a) Background Information

Deoxyribonucleic acid ("DNA") and ribonucleic acid ("RNA"), are long, thread-like macromolecules, DNA comprising a chain of deoxyribonucleotides, and RNA comprising a chain of ribonucleotides. A "nucleotide" consists of a nucleoside and one or more phosphate groups; a "nucleoside" consists of a nitrogenous base linked to a pentose sugar; a "pentose sugar" comprises five carbon atoms. In a molecule of DNA, the pentose sugar is "deoxyribose" and the nitrogenous base can be adenine ("A"), guanine ("G"), thymine ("T") or cytosine ("C"). In a molecule of RNA, the pentose sugar is "ribose", and the nitrogenous bases are the same as DNA, except uracil ("U") replaces thymine. The specific sequence of the nitrogenous bases encodes genetic information, or, the "blueprint" for life.

Double stranded DNA consists of two "complementary" strands of nucleotide chains which are held together by (relatively) weak hydrogen bonds—these bonds can be "broken" by, e.g., heating the DNA, changing the salt concentration of a fluid surrounding the DNA, or chemical manipulation; this process is referred to as "denaturation". By lowering the temperature, adjusting anew the salt concentration or removing/neutralizing the chemical, the two strands of DNA have a tendency to re-form in their approximate/identical original state. The bases of each DNA molecule selectively bind to each other: A always bonds with T, and C always bonds with G. Thus, the sequence "ATCG" of a first strand lies immediately opposite a complementary sequence "TAGC". This is referred to as "complementary base pairing" and the process of complementary base paring is referred to as "hybridization".

Three types of RNA (messenger RNA, mRNA; transfer RNA, tRNA; ribosomal RNA, rRNA) are associated with translation of the genetic information encoded in the DNA into designated amino acids, which are the building blocks for polypeptides and proteins; each of twenty naturally occurring amino acids is encoded by various groupings of three nucleotides, this grouping being referred to as a codon. Thus, the primary sequence of proteins are comprised of amino acids assembled in ribosomes based on codons defined by mRNA. Proteins are necessary to the development, maintenance and existence of living organisms; the presence, or absence, of certain proteins in different cells/tissues can be indicative of the presence, or absence of, e.g., certain biological functions of the aforementioned cells/tissues.

Genetic information is generally transferred as follows: DNA→RNA→amino acid/protein. Not every region of a DNA molecule is translated by RNA into protein; those regions that are translated are referred to as "genes." Expression of genes, therefore, serves to control the transition of hereditary characteristics by specifying the eventual proteins produced from a gene, or genes.

(b) Mutations in the Genetic Code

DNA macromolecules are chemically quite similar to each other. A and G are quite similar in chemical composition, and C, T and U are equally similar. Thus, in a specified sequence, substitutions, e.g., transitions, of an A for a G or a C for a T may occur likewise, "transversions" of an A or G for a C or T (or vice versa) may occur. When such a substitution occurs within a codon such that the amino acid encoded thereby remains the same, then the substitution can be referred to as a "silent" substitution, i.e., the nucleotides are different but the encoded amino acid is the same. However, other substitutions can alter the amino acid encoded by the codon; when the nucleotide alteration results in a chemically similar amino acid, this is referred to as a "conservative" alteration, while a chemically different amino acid resulting from the alteration is referred to as a "non-conservative" alteration. Non-conservative alterations of amino acids can result in a molecule quite unlike the original protein molecule.

A protein that has had its amino acids altered can be referred to as a "mutant", "mutation" or "variant." Mutations occur naturally and can have positive, negative or neutral consequences on the organism experiencing such a mutation. Similarly, genes that have had sections altered (e.g., by insertion or deletion of DNA sequence(s) are mutations; thus, by definition, the proteins expressed by such a mutated gene can have positive, negative or neutral consequences on the organism.

By way of example, the gene responsible for the disease cystic fibrosis (a genetically inherited disorder affecting children and young adults and which is clinically manifested by the obstruction of the airways by thick, sticky mucus and subsequent infection) comprises 250,000 nucleotides, which encode a protein of 1480 amino acids (the protein is referred to as "cystic fibrosis transmembrane conductance regulator", or "CFTR"). When this gene is compared with individuals who do not have the CF gene (i.e., individuals who have a "normal" gene), a frequent difference evidenced is that a single codon is deleted from the "normal" gene, which results in the loss of a single amino acid from the "normal" protein. However, this CFTR gene mutation accounts for only about 70% of those individuals who have CF; there are at least about 170 different CFTR gene mutations which account for the remaining 30%.

III. The Structural Formation of DNA/RNA Macromolecular Strands

While the sequence of the nitrogenous bases of the DNA and RNA macromolecule encode genetic information, the sugar and phosphate groups perform a structured role, forming the backbone of the molecule (typically, the phosphate group is attached to the fifth carbon , "C-5" or "5", hydroxyl group ("OH") of the pentose sugar). Specifically, a 3'-hydroxyl group of a first nucleotide is linked to a 5'-hydroxyl group of a second, adjacent nucleotide. The linkage between the two pentose sugars is via a phosphodiester bond. Based upon this linkage protocol, one end ("terminus") of the nucleotide chain has a 5'-terminus and the other end has a 3' terminus; linkage of two nucleotides occurs only when a hydroxyl group is present at the 3'-terminus. By convention, the base sequence of nucleotide chains is written in a 5' to 3' direction, i.e. 5'-ATCG-3' (SEQ ID NO:1) (the complementary chain is oriented in an anti-parallel fashion, i.e., the complementary chain is written in a 3' to 5' direction, i.e. 3'-TAGC-5'; SEQ ID NO:2).

The formation of the phosphodiester bond between deoxynucleotides is brought about by the enzyme "DNA-dependent DNA polymerase" (for ribonucleotides,. the enzyme is "DNA-dependent RNA polymerase"). In order for DNA polymerase to synthesize a macromolecule of DNA (i.e., "elongation" of the DNA macromolecule), the following components are required: (1) a single stranded DNA molecule, referred to as a "template"; (2) a (typically) short DNA strand, having a free 3'-hydroxyl group, which is hybridized to a specific site on the template, the short strand being referred to as a "primer"; and (3) free deoxyribonucleotide triphosphates ("dNTP"), i.e. deoxyadenosine 5'-triphosphate ("dATP"), deoxycytidine 5'-triphosphate ("dCTP"), deoxyguanosive 5'-triphosphate ("dGTP") and deoxythymidine 5'-triphosphate (typically abbreviated, by convention, as "TTP" but for purposes of consistency, abbreviated herein as "dTTP"). DNA polymerase elongates the primer in a single direction, i.e., from the 3'-end of the primer. The primer hybridizes to the template at a region where there can be the requisite complementary base pairing such that the DNA polymerase is capable of bringing about the formation of the phosphodiester bond between the 3'-hydroxyl group of the primer and an "incoming" DNTP which is complementary to the next base on the template. Thus, if the sequence of the template is 5'-ATCG-3' (SEQ ID NO: 1) and the primer is 3'-GC-5' (SEQ ID NO:3), the next nucleotide to be added to the 3'-terminus of the primer has the base A (complementary to T on the template) via the formation of a phosphodiester bond, mediated by DNA polymerase, between the dATP and the hydroxyl group of the T nucleotide on the primer. This process continues (typically) until a complete complement for the template is generated.

While the DNA polymerase enzyme functions principally to elongate a primer strand, the enzyme "ligase" functions principally to repair single-strand breaks by the formation of the phosphodiester bonds between two adjacent nucleotides which are hybridized to a unitary single strand. Thus, if the sequence of the unitary single strand is 5'-ATCG-3' (SEQ ID NO: 1) and a break, or "nick", has occurred between the A and the G of the complementary strand hybridized thereto, 3'-TA•GC-5' (where "•" indicates such a break) (SEQ ID NO: 4), the ligase enzyme can "repair" the nick by the formation of a phosphodiester bond between the A and C. Beneficially, ligase (typically) cannot mediate the formation of such a phosphodiester bond if, inter alia, one of the nucleotides is not complementary to the nucleotide on the unitary strand; i.e., if the sequence of the unitary strand is ATCG and two other strands have the sequence TA and TC (the T of the TC strand cannot hybridize to the C of the ATCG strand), ligase cannot mediate the formation of a phosphodiester bond between TA and TC.

IV. Amplification Techniques

There are currently several available techniques for the amplification of nucleic acids. A well known amplification technique is referred to as the "Polymerase Chain Reaction", or "PCR." Mullis, K., et al. "Specific Enzymatic Amplification of DNA In Vitro: The Polymerase Chain Reaction." *Cold Spring Harbor Symposia on Ouant. Bio.* 51:263–273 (1986). In the PCR protocol, the template double stranded DNA is denatured (resulting in single strands A and B, "SS-A" and "SS-B"); two primers, one having a sequence complementary to a portion of SS-A, and one having a sequence complementary to SS-B, selectively hybridize to their respective complementary strands. In the presence of DNA polymerase and dNTPs, each primer will be elongated to form complements to the original SS-A and SS-B. Thus, at the end of one such "cycle", the number of "copies" of each strand increases by two—during the next cycle, then, there are two SS-A and two SS-B, each capable of being "copied" as described above. This process is referred to as "exponential" amplificati on, which means, in essence, that with each cycle, the number of copies double. I.e., theoretically after about 20 cycles, over one million copies are generated ($2^{20}$).

Several practical problems exist with PCR. First extraneous sequences along the two templates can hybridize with the primers; this results in co-amplification due to such non-specific hybridization. As the level of amplification increases, the severity of such co-amplification also increases. Second, because of the ability of PCR to readily generate millions of copies for each initial template, accidental introduction of the end-product of a previous reaction into other samples easily leads to false-positive results. Third, PCR, does not, in and of itself, allow for detection of single-base changes, i.e. the protocol does not, in and of itself, allow for discrimi nation between "normal" and "mutational" sequences.

An a lternative to PCR is to the so-called "Ligase Chain Reaction", or "LCR". Barany, F. "Genetic disease detectio n and DNA amplification using thermostable ligase." *Proc. Natl. Acad. Sci.* 88:189–193 (1991). This technique amplifies a specific target exponentially, based upon utilization of four primers, two for each single strand of the original double stranded template. Each primer pair hybridizes in an adjacent fashion to each single strand of the template, and ligase covalently joins each primer at the region of adjacent hybridization. As with PCR, the resulting products serve as template (along with the original template) in the next cycle, thus leading to exponential amplification with each cycle. Beneficially, LCR can be utilized to detect mutations, and in particular, single nucleotide mutations—if the primers are designed as complements to the non-mutated version of, e.g., a gene, such that each primer is adjacent to a point where a known mutation can occur, and the template includes such mutation, the ligase cannot covalently couple the two primers that have hybridized thereto.

A problem associated with LCR is that, by definition, the procedure requires four primers which can result in non-specific "blunt-end ligation" of the primers without the need for the presence of target. I.e., there is preferential hybridization of the primers to their respective primer complements rather than the target sequence due to the utilization (most typically) of excess molar concentration of the primers. These double-stranded blunt-end fragments are capable of being ligated even in the absence of target DNA sequences. This can lead to high background signal or false-positive results.

Related to LCR is the so-called "Oligonucleotide Ligation Assay", or "OLA". Landegren, U., et al., *Science* 241:107–1080 (1988). The OLA protocol relies upon the use of two primers capable of hybridizing to a single strand of a target in an adjacent manner. OLA, like LCR, is particularly suited for the detection of point mutations. Unlike LCR, however, OLA does not result in exponential amplification but rather, "linear" amplification, i.e., at the end of each cycle, only a single end-product (the covalently coupled primers) is produced. A problem associated with OLA, then, is the lack of exponential amplification.

Combining PCR and OLA has been reported as a method of detection. Nickerson, D. A., et al., "Automated DNA diagnostics using an ELISA-based oligonucleotide ligation assay." *Proc. Natl. Acad. Sci. USA* 87:8923–8927 (1990). As reported, the target DNA was exponentially amplified using PCR followed by detection of the amplified target using OLA.

A problem associated with such combinations is that they inherit any problems associated with PCR, plus, by definition, multiple, and separate, processing steps are required.

Additional amplification techniques have been described. See, for example, International Publication No. WO 90/01069, "Process for amplifying and detecting nucleic acid sequences" (1990). In this protocol, as with LCR, two sets of primers are utilized; however, the primers are designed such that upon hybridization to SS-A and SS-B, "gaps" exist between the hybridized primers. These gaps are then "repaired" (filled) with complementary dNTPs (as mediated by DNA polymerase) such that when the gaps are repaired, ligase covalently joins the "repaired" primer to the other primer. Thus, at the end of each cycle, each single strand has a complement capable of serving as a target during the next cycle; thus, this procedure results in exponential amplification.

While this protocol avoids the LCR problem of non-specific blunt end ligation in the absence of target, unlike LCR this protocol does not allow for single base mutational detection. In addition, a critical difficulty in using this technique is the need to design the oligonucleotide primers such that the "gap" can be "repaired" with only a subset of the dNTPs. I.e., the gap cannot comprise all four of the bases such that only a maximum of three of the four dNTPs can be added to the reaction vessel.

The foregoing is to be considered as representative rather than exhaustive. As can be appreciated from the foregoing, however, is that certain of the benefits associated with the amplification protocols also contribute to drawbacks in utilization thereof. Ideally, then, any amplification protocol that is both sensitive (such as PCR) and specific (such as LCR) would enhance the ability to detect and amplify nucleic acid sequences.

SUMMARY OF THE INVENTION

The present invention is directed to these needs. In accordance with the invention, disclosed herein are methods for amplifying at least one specific nucleic acid sequence contained in a polynucleotide or a mixture of polynucleotides where a polynucleotide comprises a section having at least one defined nucleic acid sequence. The polynucleotide can be a single stranded target as in the case of, e.g., RNA or single strands of DNA, or double stranded target, as in the case of DNA or a DNA-RNA-hybrid. The amplification protocol disclosed herein is referred to as the End-Run Amplification reaction, or ERA.

Amplification of a double stranded polynucleotide in accordance with the invention comprises the steps of: a) treating the strands with three oligonucleotide moieties, each moiety having a defined nucleic acid sequence, where (1) the first oligonucleotide moiety is complementary to a first portion of the defined nucleic acid sequence of the first strand, (2) the second oligonucleotide moiety is complementary to a second portion of the defined nucleic acid sequence of the first strand, where the first portion and the second portion of the defined nucleic acid sequence are immediately adjacent to each other, and (3) the third oligonucleotide moiety comprises a nucleic acid sequence substantially complementary to said first oligonucleotide moiety; (b) providing conditions for occurrence of hybridization of the first moiety and the second moiety to the first strand where the first moiety and the second moiety are each of sufficient length such that each can hybridize to the first strand in a stable manner to allow for ligation of the first moiety and the second moiety to each other to form ligation product, and hybridization of the third moiety to the second strand where the hybridized third moiety is capable of being extended to form extension product; (c) providing conditions for occurrence of separation of the ligation product from the first strand and separation of the extension product from the second strand; and (d) treating the single stranded moieties of step c) with the three oligonucleotide moieties of step a) under conditions whereby the third moiety hybridizes with the ligation product to form additional extension product, and the first and second moieties hybridize with the extension product to form additional ligation product.

Amplification of a double stranded polynucleotide in accordance with the invention comprises the steps of: (a) treating the strands with three oligonucleotide moieties, each moiety having a defined nucleic acid sequence, where (1) the first oligonucleotide moiety is complementary to a first portion of the defined nucleic acid sequence of the first strand, (2) the second oligonucleotide moiety is complementary to a second portion of the defined nucleic acid sequence of the first strand, where the first portion and the second portion of the defined nucleic acid sequence are preferably spaced from between about one and about 10,000 nucleotides apart, and (3) the third oligonucleotide moiety comprises a nucleic acid sequence substantially complementary to said first oligonucleotide moiety; (b) providing conditions for occurrence of elongation of said second oligonucleotide moiety to a position immediately adjacent to said first oligonucleotide moiety such that the elongated second oligonucleotide moiety and the first oligonucleotide moiety can hybridize in a stable manner to allow for ligation of the first moiety and the elongated second moiety to each other to form gap-filled ligation product, and hybridization of the third moiety to the second strand where the hybridized moiety is capable of being extended to form extension product; (c) providing conditions for occurrence of separation of the ligation product from the first strand and separation of the extension product from the second strand; and (d) treating the single stranded moieties of step (c) with the three oligonucleotides of step (a) under conditions whereby the third moiety hybridizes with ligation product to form additional extension product, and the first and second moieties hybridize with the extension product to form additional gap-filled ligation product.

The embodiments can also be directed to single stranded nucleic acids whereby, initially, the extension product is generated after separation of the ligation product from the single strand and hybridization of the third moiety to the ligation product. Alternatively, the extension product can be generated initially, thereafter serving as a "template" for the ligation of first and second moieties.

Beneficially, at least one of the three oligonucleotide moieties can be labeled for either direct or indirect detection and/or capture of the amplified product. Additionally, two of the moieties can be part of a unitary structure such that only two oligonucleotide moieties are utilized in the amplification reaction.

The processes are repeated as often as necessary to produce a desired amount of the target copies; the preferred objective of such repetition is to generate sufficient products such that determination of the presence thereof can be readily derived. Accordingly, the present invention is particularly useful for amplifying sequences, either known or unknown, which are, e.g., indicative of a genetic disorder; in particular, the present invention is directed to the determination of the presence of single base defects in a polynucleotide sequence. As such, analysis of polynucleotide sequences for determinations of such defects which may be linked to particular genetic disease states, is particularly useful aspect of the present invention. Additionally, the present invention can be utilized for amplification of polynucleotides having a known sequence or having an unknown complete sequence, which allows for analysis (e.g., sequencing) of the amplified product.

BRIEF DESCRIPTION OF THE DRAWINGS

FIG. 9B provides a schematic representation of the Loop of 9A hybridized to a target sequence. FIG. 9C provides a schematic representation of an End-Run elongation along the ligated Blocker and Primer regions of the Loop of 9A, and FIG. 9D provides a schematic representation of the resulting target derived from FIG. 9C.

DETAILED DESCRIPTION OF PREFERRED EMBODIMENTS

Figure 1:
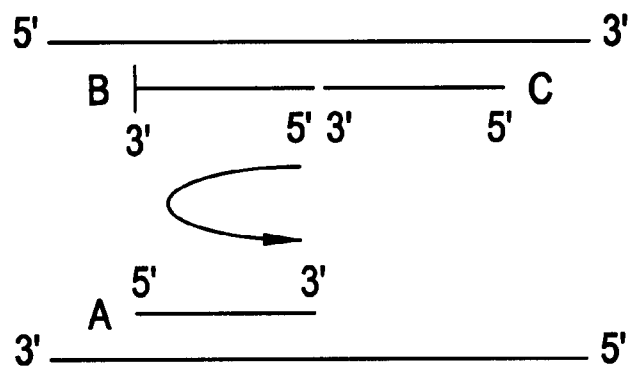
FIG. 1 provides a schematic representation of an embodiment of the components of the disclosed End-Run Amplification Reaction ("ERA") process hybridized to two target strands where the oligonucleotide moieties are as follows: A-End-Run; B-Blocker; C-Primer.

The following portion of the disclosure is directed to particularly preferred embodiments of the disclosed invention. Certain terms will be utilized for which definitional elucidation is provided—to the extent that these terms have definitions which may vary from definitions which may be utilized by those in the art, the following definitions apply.

"Blocking group" means a material added to a moiety that prevents an otherwise viable reaction. For example, an oligonucleotide which comprises a blocking group at the 3' hydroxy terminus thereof will be unable to be elongated in the 3' direction from the 3'-end. For an embodiment of the invention where a Loop oligonucleotide moiety is utilized, the Blocking group is the non-specific region which links the Blocking region of the Loop to the Primer region of the Loop.

"Complementary" means sufficient correspondence in nucleotide base pairing to enable hybridization to occur. "Substantially complementary" means sufficiently complementary to allow for stable hybridization under non-denaturing conditions. "Absolute complementary" means a one-to-one correspondence in nucleotide base pairing between two nucleic acid sequences.

"Complete Amplification Cycle" as used herein in reference to the disclosed End-Run Amplification Reaction means the ligation of at least two oligonucleotide moieties, and the extension of an oligonucleotide moiety.

"Completely denatured" means that between about 50% and about 98% of the complementary nucleic acids of two strands of polynucleotides are separated from each other.

"Elongation" means extension of an oligonucleotide hybridized to a target polynucleotide. Typically, but not always, elongation refers to extension of the oligonucleotide via incorporation of deoxynucleotide triphosphates or ribonucleotide triphosphates (wherein the target polynucleotide template is RNA) as mediated by an enzymatic reaction.

"End-Run Amplification" reaction and "ERA" are generic descriptors of the disclosed amplification reaction. ERA includes, inter alia, Nested End-Run Amplification ("NERA") and Loop End-Run Amplification ("LERA").

"Exponential" where used in conjunction with the term "amplification", refers to an approximate doubling of the number of target sequences after each cyclical event. E.g., with double stranded target sequences after the first cycle, approximately four targets are available; after the second, approximately eight targets; after the third, approximately sixteen targets; etc.

"False positive result" results from spurious amplification which has generated a detectable product that is not generated via a specific target sequence or in a target-independent fashion.

"Fill-in Reaction" refers to the elongation of an oligonucleotide through the gap region up to another oligonucleotide, where both oligonucleotides are hybridized to a target.

"Gap" means a region between two oligonucleotide moieties which have hybridized to the same strand of a target sequence. A gap may be from 1 to about 10,000 nucleotides in length.

"Gap Target Sequence" means a target sequence including a region of either partially or fully undefined nucleic acid sequence; preferably, the gap portion of the target is flanked on either side thereof by regions of defined sequence such that complementary oligonucleotide moieties can hybridize thereto, thus providing a gap between the oligonucleotides along the region of the either partially or fully undefined nucleic acid sequence.

"Label" means a moiety which is conjugated to an oligonucleotide moiety or probe such that the oligonucleotide moiety or probe can be detected or captured. A "directly detectable" label is a signal-producing label which is capable of detection either directly or through its interaction with a substance such as a substrate (in the case of an enzyme), a light source (in the case of a fluorescent compound) or a photomultiplier tube (in the case of a radioactive or chemiluminescent compound). A "proximity label" is one of at least two labels which interact with each other to produce a detectable signal when the proximity labels are brought together. Typically, a first proximity label is used in combination with a corresponding second proximity label. An "indirectly detectable" label is a substance which in and of itself does not provide a signal but which can be utilized to identify an oligonucleotide to which the indirectly detectable label is attached. E.g, biotin can be an indirectly detectable label, whereby labelled or insolubilized avidin is used in conjunction therewith—in the first instance, labelled avidin will bind to moieties comprising biotin such that the complex can be directly detected; in the second instance, the biotinylated moiety is insolubilized via the insolubilized avidin, thus allowing for separation, and hence, detection, thereof.

"Ligase" means an enzyme(s) which catalyzes the covalent attachment of two oligonucleotide moieties to one another.

"Ligation" means the covalent attachment of two or more oligonucleotide moieties. Ligation includes enzymatic processes such as those utilizing a ligase, as well as chemical processes including, but not limited to, chemical reactions, photochemical reactions (e.g. photocoupling; see, e.g. WIPO Publication No. WO 90/01069, publication date of Feb. 8, 1990 incorporated herein by reference), thermochemical and redox reactions.

"Ligation event" means that ligation of two or more oligonucleotides has occurred.

"Linear" when used in conjunction with the term "amplification" refers to an approximate unitary increase in a target sequence copy after each cyclical event. E.g., after the first cycle, one product is generated; after the second cycle, one product is generated; after the third cycle, one product is generated.

"Loop" when used in conjunction with the LERA embodiment of the invention, is an oligonucleotide moiety comprising a Blocker region, a Primer region, and a non-specific region which attaches the Blocker region to the Primer region.

"Melting temperature" and "$T_m$" refer to the temperature at which 50% of two complementary strands of DNA uncoil and separate. $T_m$ is a function of the length of single stranded DNA and the base composition thereof. Generally, for short oligonucleotide moieties (i.e. less than about 25 nucleotides) an approximate value of $T_m$ (° C.) is equal to 4(G+C)+2(A+T). E.g., for an oligonucleotide comprising 4A, 5C, 6G and 6T, the approximate $T_m$ thereof is 4(5+6)+2(4+6)=64° C.

"Oligonucleotide moiety" means a synthetic nucleic acid fragment, or any chemical moiety capable of binding to a specific nucleic acid sequence in a specific manner and serving as a substrate for, e.g., an extension reaction or ligation event; exemplary chemical moieties are the so-called "Peptide Nucleic Acids" (see Egholm, M. et al "Peptide Nucleic Acids" *J. Am. Chem. Soc.* 114/5:1895–1897 (1992), and Nielsen, P. E. et al "Sequence-Selective Recognition of DNA by Strand Displacement with a Thymine-Substituted Polyamide" *Science* 254:1497–1500 (1991), which are incorporated herein by reference). An oligonucleotide moiety typically comprises less than 150 nucleotides and/or chemical moieties. The nucleic acid can be deoxyribonucleic acid; derivatives of deoxyribonucleic acid; ribonucleic acid; or derivatives of ribonucleic acid. There are three specific oligonucleotide moieties preferably utilized for nucleic acid amplification in accordance with the disclosed invention, these being referred to herein as "Primer"; "Blocker"; and "End-Run". These can be three separate oligonucleotide moieties, or, e.g., two oligonucleotide moieties whereby, e.g., the Blocker and Primer moieties are part of a single Loop oligonucleotide moiety where the 3'-end of the Blocker region is connected, via a non-specific region, to the 5'-end of the Primer region.

"Polymerase" means an enzyme(s) which catalyzes the assembly of deoxyribonucleotides and/or the derivatives thereof into DNA, and ribonucleotides and/or the derivatives thereof into RNA.

"Spurious amplification" results in amplified produce which is not desired, i.e., spurious amplification can result from any of spurious hybridization; spurious ligation; and/or spurious elongation.

"Spurious elongation" means that at least one oligonucleotide moiety hybridizes to a region(s) along a nucleic acid sequence that is not the specific target sequence such that in the presence of, e.g., dNTPs or NTPs, and a material capable of incorporating these onto an elongating hybridized moiety, e.g., polymerase, the hybridized moiety is capable of elongating along the nucleic acid sequence.

"Spurious hybridization" means that at least one oligonucleotide moiety hybridizes to a region(s) along a nucleic acid sequence that is not a specific target sequence.

"Spurious ligation" means (1) that at least two oligonucleotide moieties hybridize to adjacent regions along a nucleic acid sequence that is not a correct target sequence, whereby the hybridized moieties are capable of being ligated to each other; and (2) that two oligonucleotide moieties might suitably hybridize to non-specific segments such that a ligation event occurs between the two oligonucleotide moieties.

"Stringency" means the combination of conditions to which nucleic acids are subject that cause the double stranded DNA or DNA-RNA hybrids to dissociate into component single strands. These conditions include, but are not limited to, pH extremes, high temperature, salt concentration, and organic solvents.

"Target Sequence" means a defined nucleic acid sequence, the presence or absence of which is desired to be detected. The target sequence can be from any source which comprises DNA and/or RNA, i.e. the source of the target sequence is not limited to mammals. Typically, two of the oligonucleotide moieties, and in particular the Blocker and the Primer, are substantially complementary to the target sequence. Preferably, the target sequence forms part of a coding region in a gene associated with a genetic disease. For many genetic diseases, such as sickle cell anemia, the presence of a genetic mutation is characterized by small changes in the coding sequence of a gene; typically, individuals who have the genetic disease in question have genes whose sequences differ by as few one nucleotide from the corresponding sequences of these who do not have the disease. The "normal" or the "mutation" gene region can serve as the target sequence. Target sequence can include a "Gap Target Sequence".

"Thermostable enzyme" means an enzyme which can catalyze a reaction at temperatures of between about 50° C. to about 100° C. Exemplary are thermostable ligase, such as that described in WIPO Publication No. WO 91/17239, publication date of Nov. 14, 1991, which is incorporated herein by reference, and thermostable polymerase, such as that described in EPA Publication No. 0258017, publication date of Mar. 2, 1988, which is incorporated herein by reference.

"Upstream" when used in relationship to an oligonucleotide moiety is relative to the 5' to 3' orientation of the target sequence to which the oligonucleotide moiety hybridizes. Thus, for a hypothetical target 5'-ACGTTTCCCC-3' (SEQ ID NO: 5) having complementary oligonucleotide moieties 3-TGCA-5' (SEQ ID NO: 6) and 3'-GGGG-5' (SEQ ID NO: 7), when both moieties hybridize to the target, the moiety 3'-GGGG-5' is referred to as being upstream of the moiety 3'-TGCA-5'.

As those in the art will appreciate, an "average" size for a gene is about 1 kilobase; a kilobase gene comprises about $10^3$ base pairs. Therefore, if one attempts to characterize a human gene using a 100 µl sample comprising 1 microgram of total human DNA, only about 300,000 molecules of that gene will be available for detection, and 300,000 molecules will be interspersed within a mixture comprising about $9 \times 10^{11}$ other similarly sized molecules. Thus, identifying and characterizing a single human gene under these circumstances require that one discriminates the individual gene from 6 million other genes. Quite literally, therefore, it is a proper analogy to compare the search for a needle in a haystack surrounded by other somewhat similar haystacks.

The embodiments of the disclosed ERA reaction all require a ligation event for amplification of a target sequence; if a ligation event does not occur, exponential amplification of the target sequence cannot occur. However, for purposes of identification of a particular nucleic acid sequence, non-amplification of the sample material is an equally important objective. I.e., for identification of, e.g., a specific, single-base mutation, two oligonucleotide moieties having a sequence complementary to the non-mutated version of the target sequence and designed to flank the mutation region will not be amenable to a ligation event if the target sequence includes the single-base mutation. Thus, in the foregoing non-limiting example, the absence of amplification can be viewed as an indicator of the presence of a mutation. As is evident, the disclosed invention can be utilized to, inter alia, amplify a target sequence and to identify the presence of a target sequence.

The following portion of the disclosure provides information regarding preferred embodiments of the oligonucleotide moieties utilized for the disclosed procedure. In setting forth the following, identifiers are provided for each of the three moieties; these are to be construed as merely providing a point of reference for ease of identification. It is to be understood, however, that irrespective of the identifiers, these are all oligonucleotide moieties as defined herein.

Those skilled in the art will appreciate that the length of an oligonucleotide moiety, which is important to the $T_m$ thereof vis-a-vis hybridization of the moiety to a complementary sequence, can be manipulated in order to increase the "speed" of hybridization of the moiety to the complementary sequence. Thus, for example, given a target sequence having two regions of defined sequence, X and Y; a first oligonucleotide having a length X' complementary to region X; and a second oligonucleotide having a length Y' complementary to region Y, the first oligonucleotide will typically hybridize under more stringent conditions to the target "faster" than the second oligonucleotide when X'>Y'. This facet of oligonucleotide hybridization is amenable to efficient exploitation for the disclosed amplification procedure.

Referring to FIGS. 1, 2 and 5A and 6B, the oligonucleotide moieties are designated as follows: A-End-Run; B-Blocker; and C-Primer. As will be delineated in detail, the most preferred order of oligonucleotide moiety hybridization to the target sequence strands are as follows: Blocker>End-Run>Primer (the symbol ">" is meant to indicate "before"). In preferred embodiments, the order can be Blocker>Primer>End-Run and Blocker>End-Run≈Primer. As is evident, it is preferred that the first moiety to hybridize to the target is the Blocker when these three oligonucleotide moieties are utilized.

Most preferably, the ratio of Blocker:Primer:End-Run within the reaction vessel is $\geq 1:1:1$. However, variations are possible. Preferably, the Blocker should be present at a concentration which is equal to or greater than the concentration of the Primer, e.g., 1.5:1 or greater. Accordingly, it is most preferred that the amount of Primer not exceed the amount of Blocker; such a situation could increase the tendency of Primer to hybridize with the target before Blocker, a scenario which must be avoided, as will be set forth in detail below. The ratio of Blocker:End-Run can vary from the preferred $\geq 1:1$ ratio without affecting the ERA protocol. The scenario to be avoided is the titration of Blocker by End-Run such that Blocker is not sufficiently available when Primer hybridizes to the target sequence. This scenario can be avoided by adjusting cycle time, reaction temperature, $T_m$, length of the moieties concentration of the target and adjusting the ratio of Blocker:End-Run. It is preferred that of these factors, the Blocker:End-Run ratio be adjusted to avoid the foregoing scenario as this factor, relative to the others, is more readily controlled. Preferably the ratio of Blocker:End-Run is about 10:1, more preferably about 5:1, and most preferably $\geq 1:1$.

All of the oligonucleotide moieties can be labelled; however, at least one of the moieties is preferably labelled. Beneficially, when the Blocker is labelled, the label can be conjugated to the 3' thereof such that the Blocker can hybridize with the target whereby elongation from the 3' end thereof is not possible; the rationale therefore will be delineated below. Exemplary labelling protocols are well known; see, e.g., EPA Publication No. 292128, publication date of Nov. 23, 1988, which is incorporated herein by reference.

The Blocker oligonucleotide moiety is designated as such because the 3' terminus thereof is most preferably incapable of elongation of target sequence in a 5' to 3' direction. I.e., in the presence of, e.g., polymerase enzyme and dNTPs, it is most preferred that a Blocker which is hybridized to a target be incapable of elongation along the target in the 3' direction. The blocking group can be any compound which accomplishes this objective. Exemplary blocking groups are di-deoxynucleotide triphosphates ("ddNTPs"), also referred to as "chain terminating" ddNTPs. As those in the art appreciate, ddNTPs differ from deoxynucleotide triphosphates in that they lack a 3' hydroxyl group. Accordingly, while ddNTPs can be incorporated into a growing oligonucleotide moiety via the 5'-triphosphate portion thereof, the absence of a 3'-hydroxyl group prevents formation of a phosphodiester bond with a succeeding dNTP (or ddNTP). Accordingly, once a ddNTP is incorporated into the Blocker at the 3' terminus thereof, elongation thereof in a 5' to 3' direction is prevented. As will be appreciated, however, any blocking group which can prevent elongation of the Blocker oligonucleotide moiety and which does not prevent hybridization of the Blocker to the target. A blocking group can include labels. With respect to a Loop oligonucleotide moiety, the Blocking group is, in effect, satisfied via the non-specific region which attaches the Blocker region of the Loop to the Primer region of the Loop.

The length of the Blocker is preferably between about 10 to about 40 nucleotides in length; more preferably between about 15 and about 35 nucleotides in length, and most preferably about 23 nucleotides in length. However, the Blocker can be as small as two nucleotides in length (where the nucleotide at the 3' end comprises a blocking moiety); the length of the Blocker, therefore, can vary depending upon the experimental needs of the investigator and a recognition that as the length decreases, the $T_m$ decreases (i.e. preferential hybridization cannot be assured). Optimization of the lengths of the Blocker, in conjunction with such needs, is considered to be within the purview of those skilled in the art. Alternatively, the $T_m$ of the Blocker can be hbetween about 37° C. and about 98° C.; more preferably between about 70° C. and about 90° C.; and most preferably about 85° C. However, as with length, the $T_m$ of the Blocker can be substantially varied, depending upon the particular needs of the investigator. As those in the art further appreciate, $T_m$ can also be adjusted vis-a-vis the G-C content of the moiety, and this can be used advantageously when the target comprises regions that allow for utilization of oligonucleotide moieties which will or will not comprise increasing amounts of G-C.

Figure 2:
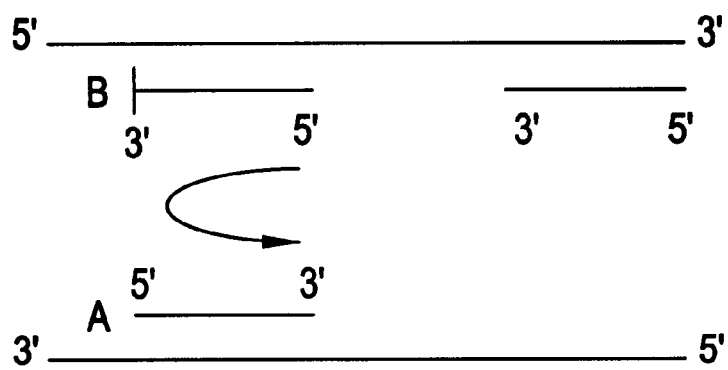
FIG. 2 provides a schematic representation of an embodiment of the components of the disclosed process hybridized to two target strands where the oligonucleotide moieties are as defined in FIG. 1.
Figure 5A:
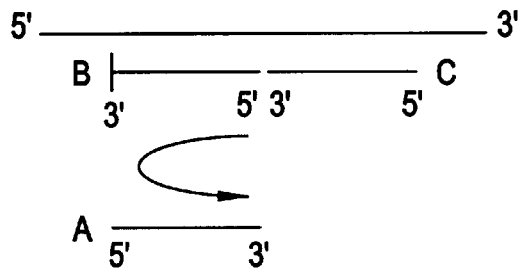
FIG. 5A and FIG. 5B provide schematic representations of an embodiment of the components of the disclosed ERA process (5A) and a schematic representation of the ERA disclosed ERA procedure (5B), where the target is single stranded and the Blocker and Primer moieties hybridize adjacent to each other.

The Primer oligonucleotide moiety is designed to hybridize upstream of the Blocker on the same strand to which the Blocker has hybridized. In an embodiment of the invention, the Primer hybridizes adjacent to the Blocker such that depending upon the target sequence, a ligation event can occur between Blocker and Primer. In another embodiment of the invention, a gap exists between the 5' end of the Blocker and the 3' end of the Primer. Thus, when hybridized to the target, and in the presence of, e.g., polymerase and dNTPs, extension of the Primer from the 3' end thereof "fills in" the gap until the extending Primer reaches the 5' end of the Blocker; at that point, a ligation event between the Blocker of elongated Primer can occur. FIG. 1 and FIG. 2 schematically depict the relative locations of Blocker and Primer in the first embodiment (FIG. 1) and the second embodiment (FIG. 2) directed to double stranded target, while FIG. 5A and FIG. 6A schematically depict the relative locations of Blocker and Primer in the first embodiment (FIG. 5A) and the second embodiment (FIG. 6A) directed to single stranded target.

With respect to the Blocker and the Primer, it is essential that the Blocker hybridize to a target sequence before the Primer—if Primer hybridizes first, in the presence of, e.g., polymerase and dNTPs, the hybridized Primer can be extended along the region of the target to which the Blocker would otherwise hybridize. I.e., even in the absence of a ligation event, a false-positive detection and amplification would result. In order to avoid this scenario, it is preferred that the length of Primer be less than about 75% of the length of Blocker; more preferably less than about 60% of the length of Blocker; and most preferably less than about 50% of the length of Blocker. Alternatively, it is preferred that the $T_m$ of Primer be less than about 75% of the $T_m$ of Blocker; more preferably less than about 60% of the $T_m$ of blocker; and most preferably less than about 50% of the $T_m$ of Blocker. By ensuring that the Primer is "shorter" than the Blocker, there is increased probability of Blocker hybridization occurring before Primer hybridization. An equivalent approach to satisfy the objective of hybridization of Blocker to the target before Primer is to add the moieties in a serial fashion with Blocker being added to the reaction mixture before Primer. When a Loop oligonucleotide moiety is utilized, because the Loop comprises Blocker and Primer regions, preferential binding is not as great a concern because, by definition, a single Loop moiety is utilized, the moiety comprising two regions which are designed to selectively hybridize to a target sequence.

As those in the art will readily appreciate, the principal differences between the embodiments is predicated upon the needs of the investigator. The embodiment of the invention depicted in FIG. 1 and FIG. 5A are most preferably directed to detection and amplification of genes which are related to genetic diseases. I.e., the Blocker and Primer are designed to flank a base or bases on the target whose deletion or alteration leads to a genetic mutation—by definition, unless the 5' end of the Blocker and the 3' end of the Primer are immediately adjacent to each other (i.e. there is exact complementarity between the moieties and the target), a ligation event will not occur. Thus, the absence of amplified product indicates, inter alia, the presence of a mutation in that target at the adjacent location of Blocker and Primer.

Figure 6A:
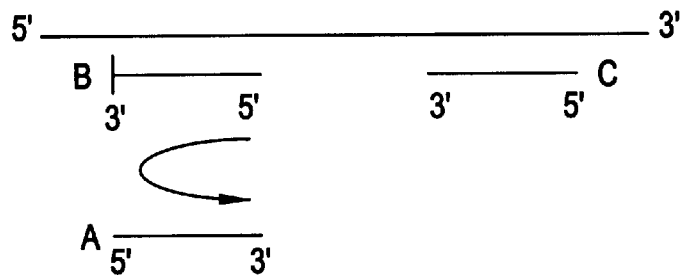
FIG. 6A and FIG. 6B provide schematic representations of an embodiment of the components of the disclosed ERA process (6A) and a schematic representation of the disclosed ERA procedure (6B) where the target is single stranded and the Blocker and Primer moieties hybridize such that a gap exists therebetween.

The embodiments of the invention depicted in FIG. 2 and FIG. 6A can also be utilized in the detection and amplification of genes related to genetic diseases. Unlike the embodiments depicted in FIGS. 1 and 5A, the Blocker and Primer need not be adjacent to each other upon hybridization to the target. Thus, by way of example and not limitation, in the case of a genetic disease having a variety of alleles caused by a variety of mutational changes in defined regions of the gene, the Blocker and Primer can be created such that they flank this region upon hybridization to the target. The gap fill-in reaction, in conjunction with the complete ERA process, amplifies the sequence complementary to the "gap" on the target—thereafter, the amplified product can be sequenced, or probes directed to each of the various mutations that can occur in the gap region can be utilized to screen the amplified product to determine which mutation is or is not present in a particular sample.

The gap between the Blocker and Primer hybridized target can be of any nucleotide length as long as the amplification cycles are regulated such that sufficient time is provided to allow for elongation of the Primer and ligation of the elongated Primer to the Blocker. However, and because it is generally preferred to decrease the time of each amplification cycle in order to maximize the production of amplified product within a reasonable time period, the distance between the 5' end of the blocker and the 3' end of the Primer when both are hybridized to the target is preferably between about 2 to about 10,000 bases, more preferably between about 2 to about 1,000 bases, and most preferably between about 2 to about 200 bases. It is, of course, evident that more than one Primer can be utilized, i.e. additional Primer(s) can be utilized which hybridize to a region of defined sequence within the gap.

The End-Run oligonucleotide moiety is designated as such because extension thereof is dependent upon a ligation event. The End-Run moiety is complementary to at least a portion of the Blocker; as is apparent, the End-Run moiety is also complementary to a portion of a strand of double stranded DNA which is complementary to the region of the other strand of double stranded DNA to which the Blocker hybridizes. Thus, the End-Run oligonucleotide moiety is equally capable of hybridizing to both the Blocker and the defined region of the complementary strand of double stranded DNA.

Because the 3' end of the End-Run moiety, unlike the 3' end of the Blocker, is not blocked, upon hybridization to a strand of target DNA, and in the presence of, e.g., polymerase and dNTPs, the End-Run moiety can be extended along that strand. Thus, it is possible for linear amplification of the strand to which the End-Run moiety hybridizes to occur. This can lead to generation of additional second strand target. From a practical perspective, this is not a critical limitation to detection: given, e.g., 20 cycles, a linear amplification has a theoretical maximum of 20 amplified products, while an exponential amplification has a theoretical maximum of nearly $1.05 \times 10^6$ amplified products. Thus, differentiation between the two can be readily accomplished.

Preferably, the End-Run moiety is complementary to a section of the Blocker moiety. One limitation which is most preferably placed upon the End-Run moiety is that the 3' end thereof does not extend beyond the 5' end of the Blocker when the two hybridize with each other: in an embodiment of the invention as depicted in FIG. 1, and situations where a ligation event cannot occur, an End-Run moiety which extends past the 5' end of the Blocker could also hybridize with a region of the 3' end of the Primer, and thus extend along the Primer; in the case of an embodiment of the invention as depicted in FIG. 2, a spurious PCR reaction can occur even in the absence of the defined target, leading to false positive results. I.e., this event might allow the Primer to "prime" an extension reaction which results in the production of a product comprising a "copy" of the End-Run moiety, if the 3' end of the End-Run overlaps and hybridizes with the 3' end of Primer, ligation between Primer and Blocker could occur, independent of the presence of a specific target.

As such, it is preferred that the total length of the End-Run oligonucleotide be between about 50% and about 100% of the length of the Blocker; more preferably between about 75% and about 95% of the length of the Blocker, and most preferably about 80% of length of Blocker. Alternatively, it is preferred that the $T_m$ of End-Run be between about 50% and about 100% of the $T_m$ of Blocker; more preferably between about 75% and about 95% of the $T_m$ of Blocker; and most preferably about 80% of the $T_m$ of Blocker. Additionally, it is most preferred that the 3' end of End-Run be flush with the 5'-end of Blocker so that the consequences of an End-Run "overhang", as described above, are effectively avoided. It is noted that the 5'-end of the End-Run need not be flush with the 3'-end of Blocker.

Figure 3:
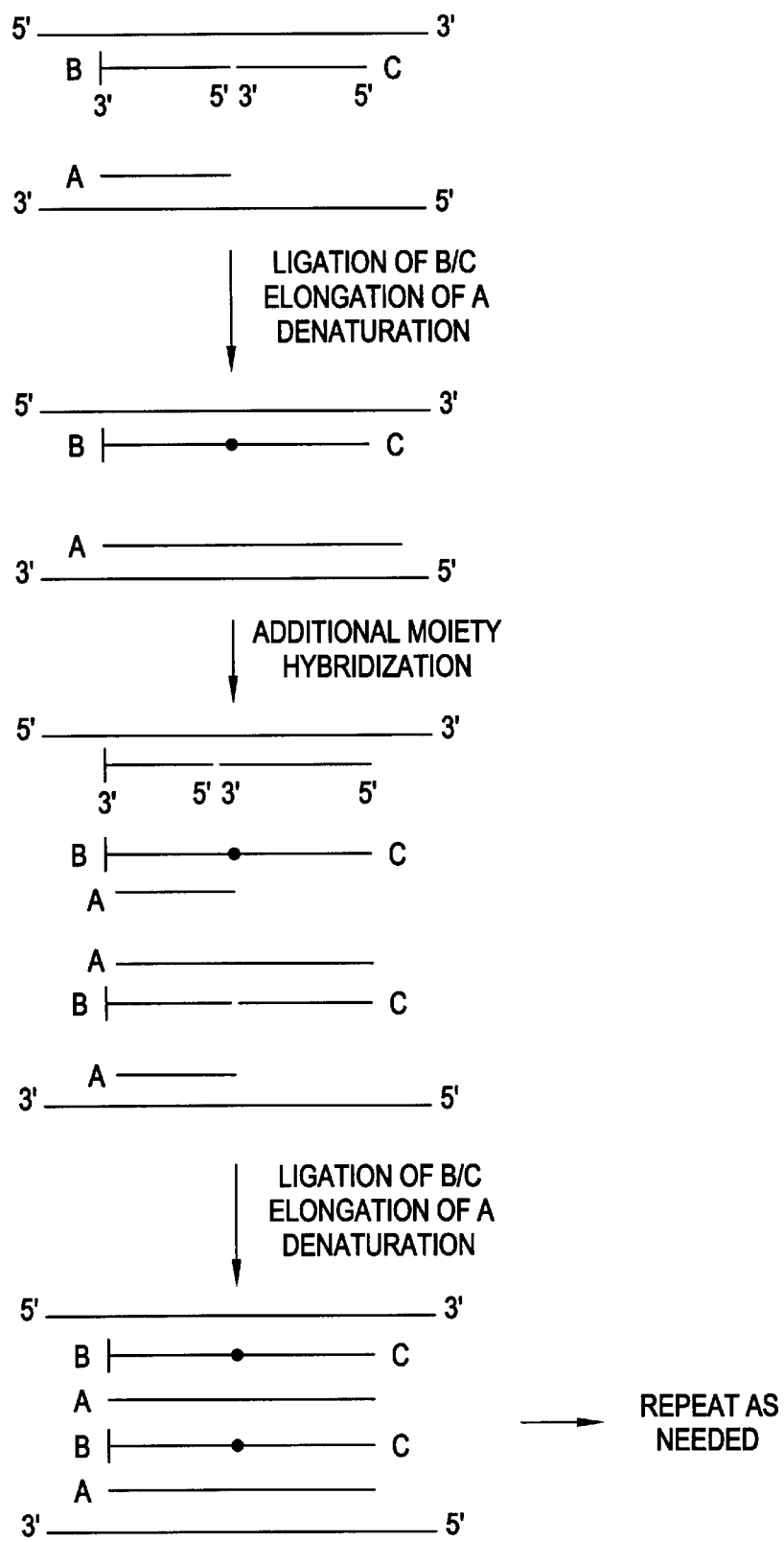
FIG. 3 provides a schematic representation of the ERA procedure as disclosed herein, using the components represented in FIG. 1.
Figure 4:
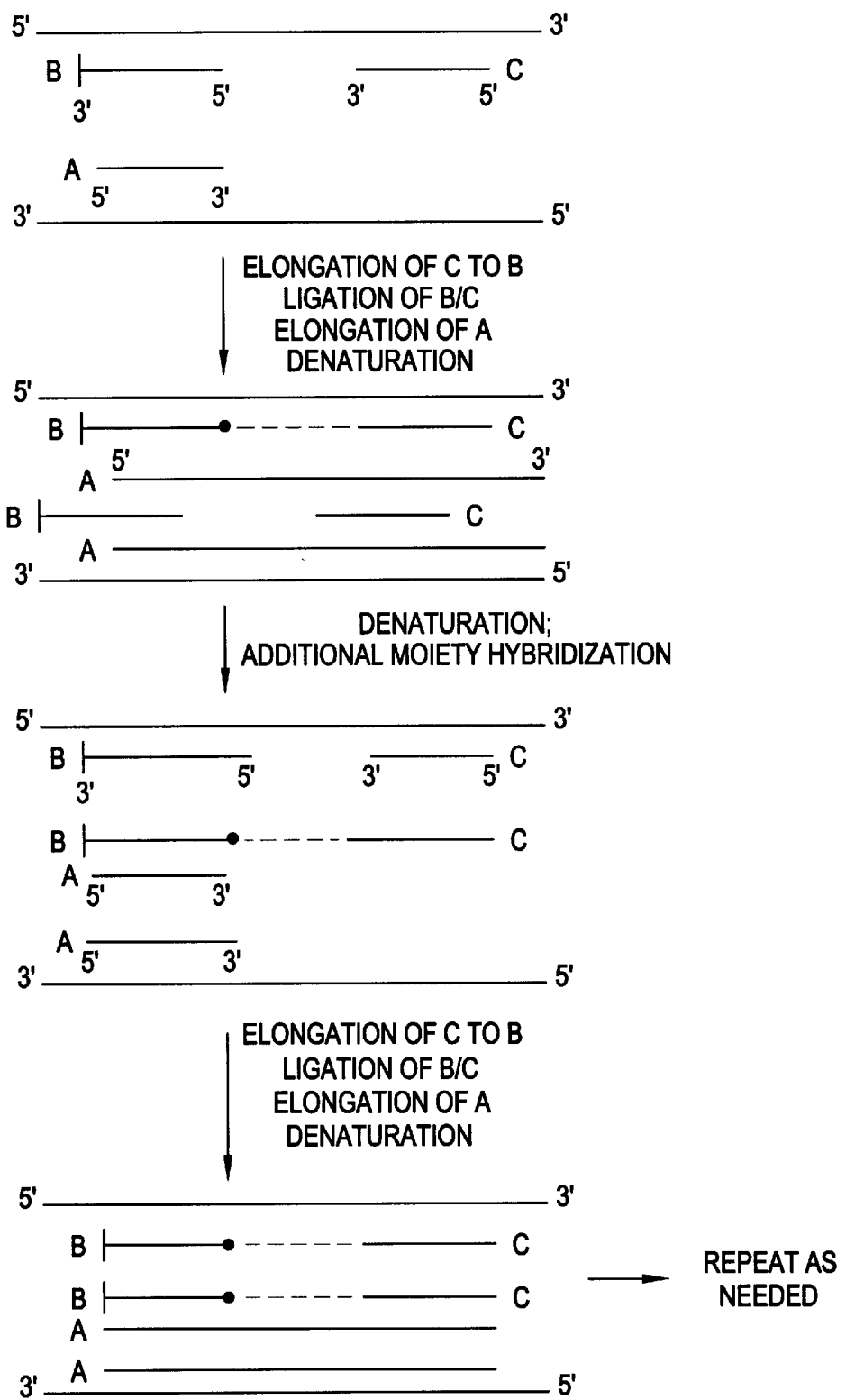
FIG. 4 provides a schematic representation of the ERA procedure as disclosed herein, using the components represented in FIG. 2.
Figure 5B:
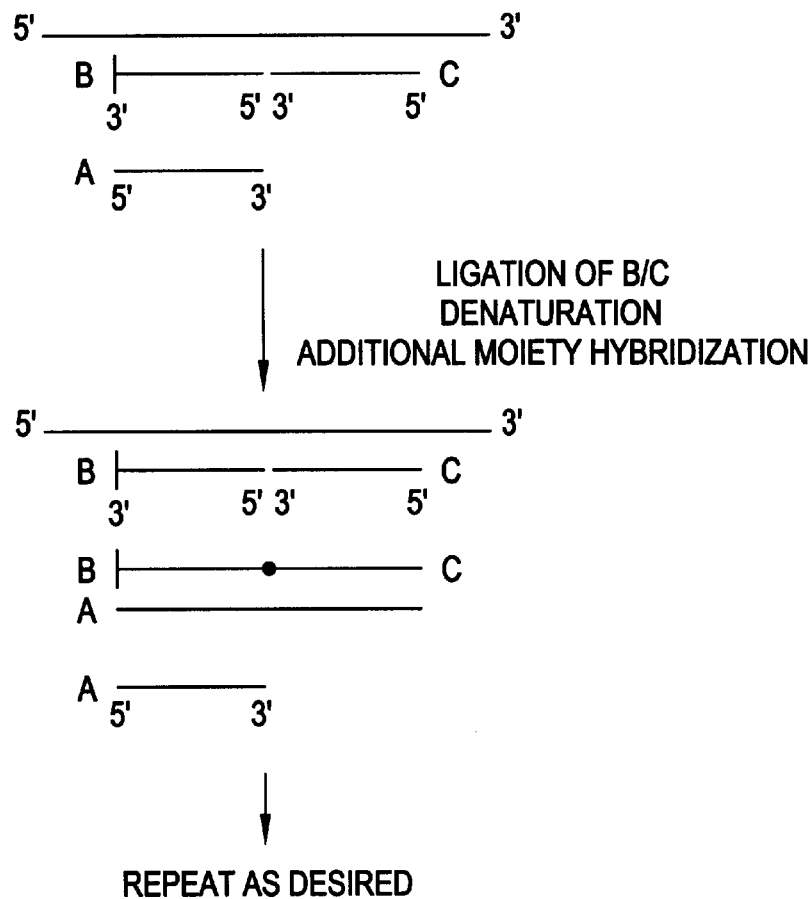
Figure 6B:
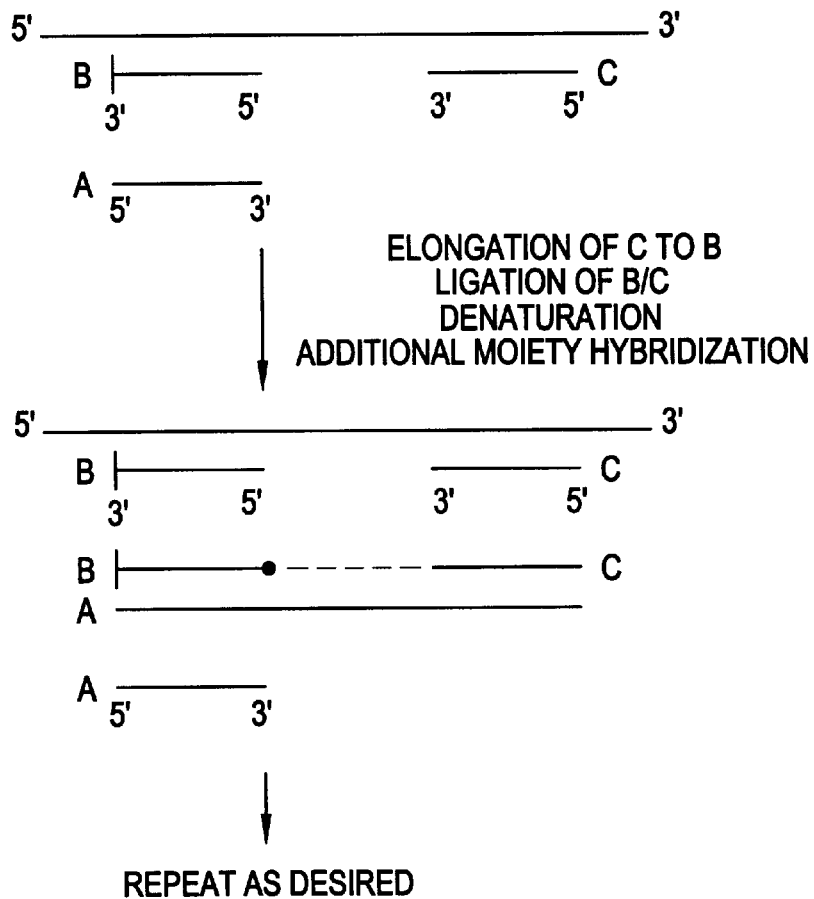

Exemplary embodiments of the amplification procedure of the present invention are particularly directed to amplification of double stranded DNA (or DNA-RNA hybrids), although amplification of RNA and single stranded DNA are equally viable. Schematic representations of the amplification procedure disclosed herein are depicted in FIG. 3 and FIG. 4. In FIG. 3, the target is double stranded DNA having a target sequence of sufficient definition such that at least two complementary oligonucleotide moieties can be generated for hybridization to at least a portion of the target sequence; FIG. 4, directed to an embodiment of the invention where the target is a gap target sequence, is similarly directed to the utilization of double stranded DNA. FIG. 5B is directed to an embodiment of the invention where the target is single stranded DNA, or RNA, where moieties B and C hybridize to the target adjacent to each other. FIG. 6B is directed to an embodiment of the invention where the target is single stranded DNA, or RNA, where moieties B and C hybridize to the target such that a "gap" is created between the hybridized moieties. The directional arrows of FIGS. 1, 2, 5a and 6a are intended to indicate the direction of the processes: i.e., the ligation event occurs, followed by elongation of the End-Run moiety along the ligation product, or an elongation event leads to a ligation event, followed by elongation of the End-Run moiety along the ligation product.

For the following portions of the disclosure, reference will be made to FIGS. 1–6 and the schematic representations of embodiments of the invention disclosed herein.

A. ADJACENT BLOCKER-PRIMER

An embodiment of the invention where the Blocker and Primer are designed to hybridize to the target immediately adjacent to each, and the amplification process related thereto, is schematically set forth in FIGS. 1 and 3 (double stranded nucleic acid) and FIGS. 5A and 5B (single stranded nucleic acid).

1. Nucleic Acid Target Sequences

The process of the disclosed invention can be utilized to produce exponential quantities of at least one defined nucleic acid sequence. In an embodiment of the invention where the Blocker and Primer hybridize immediately adjacent to each other, sufficient detail regarding at least part of the nucleic acid sequence is required such that complementary Blocker and Primer can be generated which will hybridize thereto. The Blocker and Primer need not necessarily be designed to hybridize completely along the target; rather, sufficient detail regarding the target sequence must be known such that the Blocker and Primer can hybridize thereto under stringency conditions. Alternatively, the target sequence can be isolated in sufficient quantity to enable production of sufficient oligonucleotide complementary pairs for utilization in the disclosed process.

Any source of nucleic acid can be utilized as the source of the target nucleic acid sequence; the nucleic acid sequence can be in purified or non-purified form, and these choices are principally dependent upon the needs of the investigator coupled with the objectives of the amplification. For example, for clinical evaluations, it may be impractical to purify the target sequence to complete isolation; however, to the degree that the sample is not purified, the possibility of spurious amplification, leading to potential false-positive results, may increase. With a given nucleic acid ligase or polymerase and a sample of nucleic acids of given complexity, it is well within the ability of those of ordinary skill in the art to readily adjust or determine: stringency conditions; lengths of the oligonucleotide moieties; defined length of target sequence; $T_m$ of the oligonucleotide moieties, in order to maintain the activity of the ligase and polymerase while at the same time maintaining the probability of spurious amplification to an acceptably low level.

The disclosed process may utilize either single stranded or double stranded DNA or RNA; additionally, DNA-RNA hybrids (which contain one strand of each) may be utilized. Mixtures comprising any of the foregoing may be utilized.

The target sequence to be examined can be obtained from any source, such as DNA or RNA isolated from bacteria, viruses, yeast and organisms such as plants or animals, from plasmids such as pBR322 and M13, from closed DNA or RNA. Techniques for accomplishing these tasks are considered to be within the purview of the skilled artisan. DNA may also be extracted from cells grown in tissue culture; see, for example, Maniatis et al; *Molecular Cloning, A Laboratory Manual* (New York: Cold Spring Harbor Laboratory; 1982), pp. 280–281.

Target nucleic acid sequences derived from clinical samples (e.g., skin scrapes, whole blood, serum, plasma, semen, tears, vaginal swabs, etc.) may be prepared by a variety of techniques which are available to the skilled artisan. Typically, a primary goal of these techniques is to purify the nucleic acids to a sufficient degree such that extraneous materials which might otherwise interfere with amplification of the nucleic acids are removed. For, e.g., a serum sample, preparation of the nucleic acids generally can comprise the following steps: incubate the serum for 1 hr. at 70° C. with proteinase K (Boehringer Mannheim) at 2.5 mg/ml in 25 mM MOPS (pH 6.5), 2.5 mM EDTA and 0.5% SDS. This is followed by the following extractions: phenol extraction and ether extraction. This is followed by ethanol precipitation. See, e.g., a Larzul, et al. *J. Heptol.* 5:199–204 (1987). As noted, other protocols and techniques are readily available for such purification.

2. Blocker/Primer/End-Run

Preferably, the oligonucleotide moieties are oligodeoxyribonucleotide moieties; however oligoribonucleotide moieties, or moieties comprising derivatives of deoxyribonucleotides and/or ribonucleotides may also be utilized.

The Blocker, Primer and End-Run moieties must each be of sufficient length to hybridize to the target sequence(s); therefore, the length of the moieties can vary from as little as about two nucleotides to as many as hundreds of nucleotides. More than one set of Blocker, Primer and End-Run moieties can be utilized as long as these are capable of amplifying different specific nucleic acid sequence(s).

Specific parameters regarding preferred lengths and $T_m$ of the Blocker, Primer and End-Run moieties are disclosed in detail above. In a particularly preferred embodiment, lengths (in nucleotides) are as follows: Blocker—23; Primer—10; End-Run—18. In a particularly preferred embodiment, $T_m$ (in ° C.) are as follows: Blocker—85; Primer—45; End-Run—75.

Blocker, Primer and End-Run may be prepared using any suitable method using, e.g., the methods described in Beaucage, S. et al, *Tetrahedran Letters* 22:1859–1862 (1981). Commercially available instruments capable of generating oligonucleotide moieties are preferred, as these are widely utilized and typically time and cost effective. Exemplary instruments capable of generating defined oligonucleotides include, but are not limited to, the OLIGO 1000™ (Beckman Instruments, Inc., Fullerton, Calif.); Gene Assembler™ (Pharmacia, Uppsala, Sweden); Biosearch 8750™ (Milligen Biosearch, San Rafael, Calif.); and the ABI PCR Mate™ (ABE, Foster City, Calif.).

3. Strand Separation/Denaturation

Strand separation can be accomplished using any suitable denaturing method; these include utilization of physical, chemical or enzymatic means. A physical method of strand separation involves heating the nucleic acid until it is completely denatured; heat denaturation typically involves utilization of temperatures ranging from about 80° C. to about 105° C. (preferably about 95° C.) for between about 1 to about 10 minutes (preferably about 4–5 minutes). An additional physical method of strand separation involves altering the pH of the medium in which the double strands are located; pH denaturation typically involves utilization of a pH range of from about pH 11 to about pH 14 for between about 1 second to about 10 minutes. An enzymatic method of strand separation can rely upon utilization of enzymes referred to as helicases or the enzyme RecA, which has helicase activity and in the presence of ATP has been reported to denature double stranded DNA. Reaction conditions suitable for separating the strands of nucleic acids with helicases are set forth in *Cold Spring Harbor Symposia on Ouantitative Biology*, Vol. XLIII, "DNA Replication and Recombination (New York: Cold Spring Harbor Laboratory, 1978), B. Kuhn et al., "DNA Helicases", pp. 63–67, which is incorporated herein by reference. When heat denaturation is utilized (as is preferred), enzymes utilized in the ERA protocol are most preferably thermostable enzymes.

4. Procedural Steps

Preferably, the ERA reaction takes place in a buffered aqueous solution, preferably having a pH of between about 6.0 and about 9.0. Preferably, the reaction buffer comprises various components which allow for the efficient and specific cycling of the ERA reaction. A particularly preferred buffering solution is 20 mM tris hydroxymethyl amino methane hydrochloric acid ("TRIS-HCl"), pH 7.8. Additional materials are preferably added to the reaction buffer; these materials are selected such that the cycling of the reaction is at high efficiency (e.g., the greatest amount of product per target template, preferably greater than 2x, more preferably $x^y$, and most preferably about $x^2$, where x is the number of target templates available during each cycle, and Y is greater than 1.0 but less than about 2) and high specificity (i.e., the correctness of the fidelity of the ligase and polymerase enzymes, where "polymerase fidelity" is defined as the preference of the enzyme to catalytically incorporate the correct nucleotide and "ligase fidelity" is defined whereby ligase activity is limited to nick-closing activity, e.g., ligation of two complementary oligonucleotide moieties that are adjacent to each other when hybridized to a target sequence); processivity is maximized; catalytic stability of the enzyme(s) is maintained; and reaction stability (i.e. reaction components are maintained in solution; non-specific activity is decreased; adhesion of reaction components to the surface of the reaction vessel is minimized, etc.) is maintained. For the ERA protocol disclosed herein, the following components and amounts (final concentration) have been found to accomplish these goals: 20 mM potassium chloride; 2.0 mM magnesium chloride; 5.0 mM dithiothretiol ("DTT"); 50 µM nicotinamide adenine dinucleotide ("NAD$^+$"); 50 µg/ml bovine serum albumin; and 0.1% of a non-ionic detergent (e.g., Triton x 100™). These materials can be readily varied and adjusted depending upon the specific enzymes utilized; those skilled in the art are credited with readily selecting and optimizing such materials. Other materials, such as preservatives and the like, can optionally be added to the reaction buffer. It is most preferred that double deionized water be utilized to achieve a desired final volume of the reaction buffer.

Typically, the temperature of the vessel is maintained at between about 30° C. and about 90° C., most preferably about 65° C. When heat denaturation is utilized, the temperature may increase above these values during the denaturation step. When heat denaturation is utilized (as is preferred), thermocyclers capable of providing a temperature controlled environment to the reaction vessel within a cyclical range of temperatures are preferably utilized. Exemplary is the Perkin Elmer 480™ thermal cycler.

Most preferably, Blocker, Primer and End-Run are simultaneously added to the reaction vessel. However, the moieties can be added serially, or in groups. When the moieties are added serially, it is preferred that the following orders be utilized: Blocker, End-Run, Primer; Blocker, Primer, End-Run; Blocker, End-Run and Primer; Blocker and Primer, End-Run; or Blocker and End-Run, Primer. Alternatively, the moieties can be added in any order or as a single admixture when the reaction vessel (comprising the target sequence) is maintained at about 4° C.—as those in the art appreciate, at this temperature, hybridization, and enzymatic activity, is substantially, and typically completely, prevented.

Because the lengths (and/or $T_m$) of oligonucleotide moieties are designed to increase the probability that target hybridization will occur in the following order, Blocker>Primer>End-Run, the moieties are added in approximate equimolar concentration since they are expected to react stoichiometrically. Each moiety is present in a concentration ranging from about 10 nanomolar (nM) to about 400 nM; preferably from about 50 nM to about 300 nM; and most preferably about 100 nM. The optimum quantity of probe used for each reaction also varies depending on the number of amplification cycles which are performed. Optimum concentrations can be readily determined by those of ordinary skill in the art.

Generally, as is appreciated by those in the art, the stringency of conditions is dependent upon temperature, buffer(s) and related parameters; however, the temperature parameter is typically easiest to control and therefore is a preferred stringency parameter which when varied, can be utilized to optimize varied in the performance of ERA. As noted, directly related to stringency mediated by temperature is oligonucleotide moiety length—thus, the stringency conditions can be readily optimized by those in the art in accordance with the objective of having the Blocker moiety hybridize to the target before the Primer moiety hybridizes with the target.

Because ERA is dependent upon a ligation event, it is preferred that the next step in the procedure is the ligation of Blocker and Primer hybridized to the target. Thus, the means for covalently coupling the two moieties, preferably a ligase enzyme and most preferably a thermostable ligase enzyme, is present in the reaction vessel before, during or after the moieties are admixed with the target sequence. Most preferably, the covalent coupling moiety is added to the reaction vessel after the oligonucleotide moieties have been added thereto.

The next preferred step in the reaction is the elongation of the End-Run moiety hybridized to either a target strand or a covalently coupled Blocker-Primer strand. Thus, the means for elongation of the End-Run moiety, preferably a polymerase enzyme in conjunction with deoxyribonucleotide triphosphates (i.e. dATP, dGTP, dCTP and dTTP) and/or ribonucleoside triphosphates (i.e., ATP, GTP, CTP and UTP), is present in the reaction vessel before, during or after the moieties are admixed with the target sequence. Most preferably, the polymerase enzyme is a thermostable polymerase enzyme. A most preferred additional step involves admixing the polymerase to the reaction vessel which already includes the target sequence, dNTP, and oligonucleotide moieties.

In a particular preferred protocol, all of the reagents are admixed in a reaction vessel, the temperature of which is such that hybridization and enzymatic activity is substantially prevented. This can be readily accomplished by adding the reaction components to a vessel that is maintained at about 4° C.; at this temperature, most, if not all, of the enzymatic activity is substantially prevented.

A most preferred order of adding the reactant components is as follows: reaction buffer; target sequence; dNTPS; oligonucleotide moieties; thermostable ligase enzyme; thermostable polymerase enzyme. Most preferably, the thermostable polymerase enzyme is added after a "hot start", i.e., a first "denaturation cycle" is utilized before the polymerase enzyme is added to the reaction vessel. As stated, most preferably, these components are maintained at approximately 4° C. until initiation of the amplification process is desired. The reaction components can be added to the reaction vessel manually or by means of a robotic, automated laboratory workstation capable of automatically adding a variety of reaction components to a reaction vessel(s). A particularly preferred robotic, automated laboratory workstation is the BIOMEK® 1000 (Beckman Instruments, Inc., Fullerton, Calif.).

After the reaction components are admixed, if, as is most preferred, the reaction vessel has been maintained at 4° C., the reaction vessel is subjected to a "hot start", i.e., the temperature is increased to about 95° C. for about 5 min., in order to completely denature the target sequence prior to initiation of ERA by the addition of polymerase enzyme. This is preferably followed by the amplification cycles. In any particular cycle, it is desired that at least one ligation event occurs between a Blocker and Primer hybridized to a target, and at least one elongation of an End-Run moiety hybridized to a target and/or a Blocker-Primer ligation product—however, as the amplification is substantially exponential, the number of such events dramatically increases after each cycle.

A cycle requires annealing of the oligonucleotide moieties to their respective targets, and denaturation therefrom. Thus, if denaturation is mediated by temperature (as is most preferred), the cycles are regulated by adjusting the temperature of the reaction vessel. If a non-thermostable enzymes are utilized, then as the temperature necessary to denature the strands is achieved, it is substantially possible for the enzymatic activity of the enzymes to be destroyed; thus, fresh enzyme must be added after each cycle. It is principally for this reason that thermostable enzymes are preferably utilized.

The temperature utilized within each cycle is principally dependent upon the $T_m$ of the oligonucleotide moieties; the skilled artisan is readily credited with the ability to optimize the time and temperatures utilized in each cycle. For oligonucleotide moieties between about 6 to about 10 bases in length, the $T_m$ thereof is about 40° C.; at this temperature, heat-sensitive (i.e. non-thermostable) enzymes are active. However, as the length of the moieties increase, the $T_m$ increases, thus necessitating the use of thermostable enzymes or the addition of heat-sensitive enzymes after each cycle. For the most preferred oligonucleotide moiety lengths (Blocker—23 bases; Primer—10 bases; End-Run—18 bases), each cycle is most preferably defined by the following parameters: 95° C.—1 minute; 70° C.—4 minutes; 40° C.—4 minutes.

If other means of denaturation are utilized, such as physical means, enzymatic means, pH adjustment, or chemical means, the skilled artisan will appreciate that the means must be compatible with the reaction components. Optimization of such means with the components necessary to conduct the ERA protocol are considered to be within the purview of the skilled artisan.

The number of cycles is principally dependent upon the needs of the investigator. Typically, detectable results can be achieved after as little as between about 10 to about 20 cycles. However, cycles in excess of 20 can be utilized. One quasi-limitation on the number of cycles is the amount of oligonucleotide moieties, dNTPs and enzyme utilized. After increasing cycles, these components will eventually be depleted such that additional cycles will not lead to additional amplification. Thus, as the desired number of cycles increases, it is preferred that the relative amounts, of oligonucleotide moieties, dNTPs and enzymes increase; optimization thereof vis-a-vis the desired number of cycles, is considered to be within the skill of those in the art.

After the appropriate number of cycles is performed, the reaction may be stopped. An efficient manner is to inactivate the enzyme and this can, most preferably, be accomplished by lowering the temperature of the reaction vessel to 4° C. However, other approaches can be utilized, e.g., EDTA and a urea "stop" dye. Additionally, the enzymes can be chemically inactivated using methods known to those in the art, or the components can be separated: on, e.g., Sephadex™ columns; by filtration; by centrifugation; or by gel electrophoresis. Most preferably, the reaction is terminated by utilization of temperature.

A potentially fatal problem associated with any amplification protocol is contamination; this problem is particularly acute when the amplification protocol is being utilized for diagnostic purposes. For example, even modest contamination from one reaction vessel can lead to erroneous positive results, i.e., a desired target, which is present in first vessel but not in a second vessel, may be accidently transferred from the first vessel to the second vessel—thus, the second vessel will evidence amplification of the desired target when, in fact, that target was not originally present in the second vessel. Various approaches for substantially reducing the possibility of such contamination have been proffered. One such approach involves utilization of the enzyme uracil-N-glycosylase ("UNG"). UNG degrades uracil such that oligonucleotides comprising uracil, in the presence of UNG, are effectively degraded. Additionally, UNG can be inactivated with heat (i.e., about 80° C.). Thus, when concerns regarding contamination are attenuated, a preferred solution is to replace dTTP with UTP in the reaction mixture, such that the amplified products incorporate uracil in lieu of thymidine. After amplification of the target in the first vessel, UNG is added to the second vessel; if any amplified product from the first vessel has contaminated the second, the UNG will effectively degrade the contaminant. Thereafter, the second vessel is "hot-started" by heating the vessel to about 80° C., thereby inactivating the UNG. Thereafter, the dNTPs and/or enzymes can be added to the second reaction vessel for initiation of the ERA protocol.

5. Oligonucleotide Labelling

Labelling of the oligonucleotide moieties is discretionary and principally dependent upon the needs of the investigator. Preferably, the label is one that is capable of being readily manipulated and amenable to efficient detection. Any or all of the oligonucleotide moieties can be labelled. Additionally, the dNTPs can be labelled.

Approaches involving directly detectable labels include utilization of, e.g., dNTPs labelled with radioactive labels such as $^{32}P$, $^{35}S$, or $^{125}I$ which are incorporated into the oligonucleotide moieties or which are utilized vis-a-vis elongation of the End-Run moiety. However, when the latter approach is utilized, separation of the incorporated from the unincorporated labelled dNTPs is required. Approaches for direct labelling of oligonucleotides are well known in the art. A particularly preferred approach is the "end-labelling" approach whereby T4 polynucleotide kinase is used to introduce a 5'-end label by the transfer of the γ-phosphate from a ribonucleoside 5'-triphosphate donor (typically [γ-$^{32}P$]ATP) to the 5'-hydroxyl of the oligonucleotide. See, e.g., Richardson, C. C., *The Enzymes*, Vol. XIV, Nucleic Acids Part A, Ed. Boyer, P. D. Acad. Press, p. 299, 1981. Alternatively, terminal deoxynucleotidyl transferase can be utilized to add a series of supplied deoxynucleotides onto the 3'-end of the oligonucleotide; single nucleotide labelling is possible using, e.g., [$\alpha^{32}P$] deoxy NTP. See, e.g. Bollum, F. J. *The Enzymes*, Vol. X, Ed. Boyer, P. D. Acad. Press, 1974; Yousaf, S. I., et al *Gene* 27:309 (1984); and Wahl, G. M. et al *PNAS USA* 76:3683–3687 (1979). Labelled ddNTPs, e.g., [$\alpha^{32}P$] ddATP, can also be utilized.

Alternatively, non-radioactively labelled oligonucleotides, such as hapten labelled oligonucleotides, are viable. See, e.g., WIPO Publication No. WO 91/19729 "Nucleic Acid Probes and Protein Probes" Adams, C. W. Publication Date of Dec. 26, 1991, which is incorporated herein by reference. A detection scheme involving such hapten-labels includes utilization of antibodies to the hapten, the antibodies being labelled.

A similar approach involves utilization of biotin and avidin, or the derivatives thereof. For example, biotin-11-dUTP can be utilized in lieu of dTTP, or biotin-14-dATP in lieu of dATP; labelled avidin, or the derivatives thereof, can then be utilized for detection. See, generally, Langer, P. R. et al, *PNAS USA* 78:6633–6637 (1981), which is incorporated herein by reference. Biotinylated phosphoramidites can also be utilized. See, e.g., Misiura, K. et al. *Nucl. Acids. Res.* 18:4345–4354 (1990), which is incorporated herein by reference. Such phosphoramidites allows for precise incorporation thereof at desired locations along the growing oligonucleotide moiety during the synthesis thereof.

Additionally, fluorescein-11-dUTP (see Simmonds, A. C. et al *Clin. Chem.* 37:1527–1528 (1991), incorporated herein by reference) and digoxigenin-i dUTP (see Muhlegger, K. et al. *Nucleosides & Nucleotides* 8:1161–1163 (1989), incorporated herein by reference) can be utilized as labels.

Chemiluminescent substrates are also viable as labels. For example, horseradish peroxidase ("HRP") and alkaline phosphatase ("AP"), both of which can be directly cross-linked to nucleic acids (see, Renz, M. and Kurz, C. *Nucl. Acids Res.* 12:3435–3444 (1964), incorporated herein by reference) can be utilized as enzyme labels. Luminal, a substrate for HRP, and substituted dioxetanes, substrates for AP, can be utilized as chemiluminescent substrates. Exemplary of the HRP labelling protocol is the ECL system available from Amersham (Arlington Heights, Ill., USA).

In a research environment, where target amplification is not always performed on a continuing basis, utilization of radioactive labels may be preferred. In a non-research environment, e.g., in a clinical setting, such labels may not be preferred due to the disposal problem and allied risks associated with continued exposure to radioactive labels. Thus, non-radioactive labels may be preferred in these settings. Thus, the foregoing should not be construed as limiting, but rather as exemplary.

6. Detection of Amplified Product

Detection of the amplified product is primarily dependent upon the label(s) utilized. The skilled artisan is credited with the ability to select an appropriate detection protocol vis-a-vis the selected label.

By way of example, and not limitation, when radioactive labels are utilized, it is preferred that the amplified product and reaction components from the reaction vessel be subjected to some form of separating technique before detection, preferably "slab" gel electrophoresis; thereafter, x-ray sensitive film can be placed upon the separating medium whereby exposure thereof via the radioactive label evidences whether or not product amplification has occurred. Alternatively, the amplified products can be separated from the reaction components and radioactive counts can be measured using instruments adapted or designed for such measurements.

Non-radioactive labels can be visually identified or detected with instruments designed for such purposes. For example, if the label is an enzyme such as HRP and the substrate is a chromogenic material, the introduction of the substrate to the label can result in a color change, whereby the color provides evidence of the amplified product. Haptenic labels can be detected using anti-hapten antibodies having a detectable label(s) conjugated thereto.

For indirectly detectable labels, such as biotin, detection can be accomplished using avidin (or derivatives thereof) having a detectable label(s) conjugated thereto, or by capture and separation from the reaction admixture.

A further means for detection of amplified product includes utilization of nucleic acid probes which are complementary to the amplified product. For this type of detection, labelling of the oligonucleotide moieties is not necessary. If the target is present, amplification thereof will result in sufficient amounts of the target such that labelled nucleic acid probes can be used for detection. Single probes comprising directly or indirectly detectable labels can be utilized, or multiple probes comprising a directly or indirectly detectable label and capture moieties can be utilized. See, for example, U.S. Ser. No. 07/576,137 "Solution Phase Nucleic Acid Hybridization and Solid Phase Capture For Detection of Target Nucleic Acid, and Kit Therefore," which is incorporated herein by reference.

B. GAP Between Blocker-Primer

An embodiment of the invention where the Blocker and Primer are designed to hybridize to the target such that upon hybridization a gap exists between the Blocker and Primer, and the amplification process related thereto, is schematically set forth in FIGS. 2 and 4 (double stranded nucleic acid) and FIGS. 5A and 5B (single stranded nucleic acid).

1. Nucleic Acid Target Sequences

The information set forth in Section A.1 is applicable to this embodiment of the invention. However, by definition, the information regarding the sequence between the gap need not be known. For example, the sequence of the gap can be unknown; what is necessary is that sufficient detail regarding portion(s) on either side of the gap must be known such that complementary Blocker and Primer can be generated.

2. Blocker/Primer/Rnd-Run

The information set forth in Section A.2 is applicable to this embodiment of the invention. Additional Primer can be utilized (for convenience, referred to as "Primer.A"). Primer.A can be designed to hybridize to a portion of the gap having a sequence of sufficient definition. Thus, if the gap is exceedingly large (i.e., greater than about 10,000 nucleotides), it may be desirable, if possible, to utilize a Primer.A to hybridize to, preferably, the approximate middle of the gap in order to effectuate the elongation of the Primer, through Primer.A (after covalent attachment of elongated Primer and Primer.A), through Blocker and covalent attachment of elongated Primer.A and Blocker.

3. Strand Separation/Denaturation

The information set forth in Section A.3 is applicable to this embodiment of the invention.

4. Procedural Steps

The information set forth in Section A.3 is applicable to this embodiment of the invention. It is noted that the amplification of a gap target sequence is also dependent upon a ligation event—however, as this embodiment of the invention is particularly suited for amplification of target sequence(s) comprising a region(s) of fully or partially unknown sequence, the ligation event occurs after elongation of the Primer(s) up to a point immediately adjacent to the Blocker, whereupon a ligation event can occur.

For gaps exceeding about 200 nucleotides in length, it is preferred that the reaction time for each cycle be increased; preferably, each cycle should be greater than about 10 minutes, i.e. greater than about 12–15 minutes. The intent of such increase is to increase cycling efficiency.

5. Oligonucleotide Labelling

The information set forth in Section A.4 is applicable to this embodiment of the invention.

6. Detection of Anplified Product

The information set forth in Section A.5 is applicable to this embodiment of the invention. Particularly preferred detection schemes involve utilization of nucleic acid probes which are complementary to one (or more) of the oligonucleotide moieties; this would allow for "pulling" amplicons from the reaction vessel, whereby sequencing thereof can be accomplished.

In diagnostic applications involving this embodiment of the invention provides the opportunity to utilize a variety of labelled probes directed to specific mutations that lead to one or more alleles. I.e., for a variety of mutations known to exist within a particular region of a gene, the Blocker and Primer(s) can be designed to flank this region; amplification of the target will then generate amplicons of undefined mutations. Specific probes directed to the known mutational sequences can then be utilized to screen the amplicons such that, depending on which probe hybridizes with the amplicons, identification of the mutation can be accomplished. Those skilled in the art are credited with the ability to optimize the conditions necessary for screening of amplified targets as delineated above.

C. Nested End-Run Amplification Reaction ("NERA")

Figure 7:
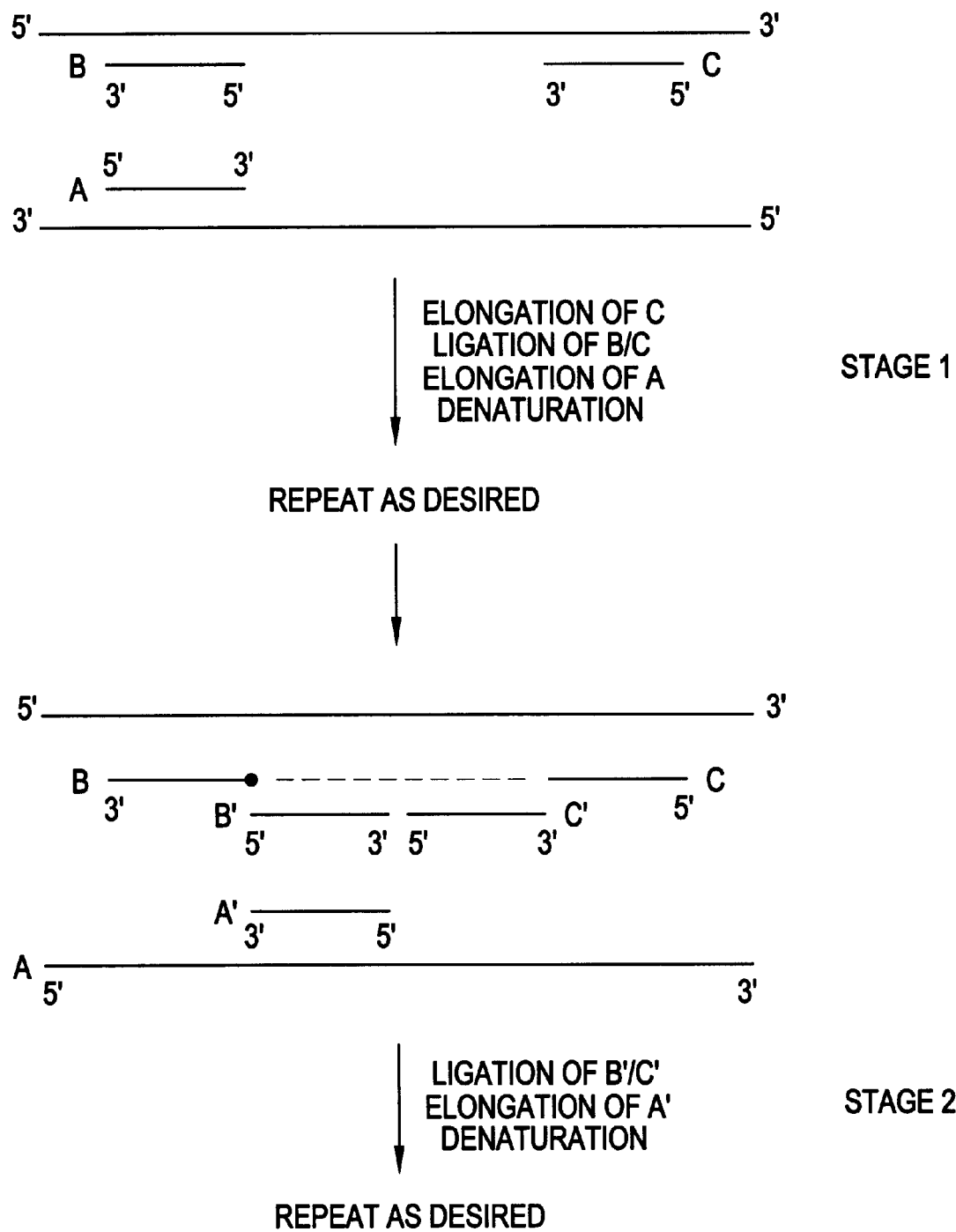
FIG. 7 provides a schematic representation of an alternative embodiment of the invention designated Nested End-Run Amplification Reaction ("NERA"), where the target is double stranded.

An embodiment of the ERA protocol which relies upon "hybrid" adjacent Blocker-Primer and GAP Blocker-Primer is referred to as Nested End-Run Amplification Reaction ("NERA"). NERA is preferably a two stage amplification reaction: the first stage is designed to amplify a target sequence including a quasi-gap, i.e. a region in the target sequence between a hybridized Blocker and Primer that has a sequence which is substantially identified; the second stage is designed to amplify the quasi-gap of the first stage using, most preferably, nested Blocker and nested Primer which hybridize adjacent to each other. The purpose of NERA is to provide a protocol for determining whether or not spurious amplification has occurred. The NERA protocol is schematically set forth in FIG. 7 (double stranded target) of FIG. 8 (single stranded target).

In the ERA disclosed in Section I.B., supra, it is possible that along the entire range of the target sequence, Blocker and Primer may hybridize to complementary regions which do not flank the desired gap region—the ensuing elongation of Primer and covalent coupling of elongated Primer to Blocker, along with elongation of End-Run, could result, in this situation, in spurious amplification. The nested oligonucleotide moieties are designed with this possibility and in an effort to advantageously avoid this scenario.

In the first stage of NERA, Blocker, Primer and End-Run moieties as utilized are disclosed in Section I.B.—i.e., the Blocker and Primer are designed to flank a gap section which is amenable to Primer elongation and a ligation event between elongated Primer and Blocker, followed by elongation of End-Run. For NERA, the sequence of the gap segment must be substantially identified as will be made apparent below. The first stage of NERA, in essence, follows the protocol disclosed in Section I.B., i.e., a putative target sequence(s) is exponentially amplified in a quantity sufficient for further evaluation.

The second stage of NERA utilizes the amplified product of the first stage for target sequences; in the second stage, nested Blocker, Primer and End-Run moieties are admixed with the amplified product from the first stage (along with, inter alia, ligase and polymerase enzymes and dNTPs). The nested Blocker and Primer are designed to hybridize with the fill-in portion of the gap of the original target. Herein lies a solution to the problem occasioned by spurious amplification from the first stage. If, for example, Blocker and Primer hybridized to non-specific "target" regions in the first stage, spurious amplification will result; in this situation, the filled-in gap will not be, by definition, the desired target gap to which the nested Blocker and Primer are designed to hybridize. Thus, it is statistically unlikely that the nested Blocker and Primer will be capable of hybridizing with the amplified product created from the first stage. This is because it is improbable that to the degree that Blocker and Primer hybridize to non-target regions on the polynucleotide, the gap region occurring within the non-target region will include adjacent sequences which, when filled-in, will be complementary to the nested Blocker and Primer.

Accordingly, NERA allows for readily determining if spurious amplification has occurred when Blocker and Primer are designed to create a gap upon hybridization to the target. In a non-spurious amplification scenario, i.e. where the Blocker and Primer hybridize to a desired portion of the target sequence, the resulting amplified product serves as target for the nested moieties in the second stage; because the "correct" target, including the "correct" gap (having a defined/partially defined sequence) has been amplified, during the second stage, the nested Blocker and Primer moieties are capable of hybridizing to the amplified filled-in region, along with ligation thereof and extension of End-Run.

Figure 8:
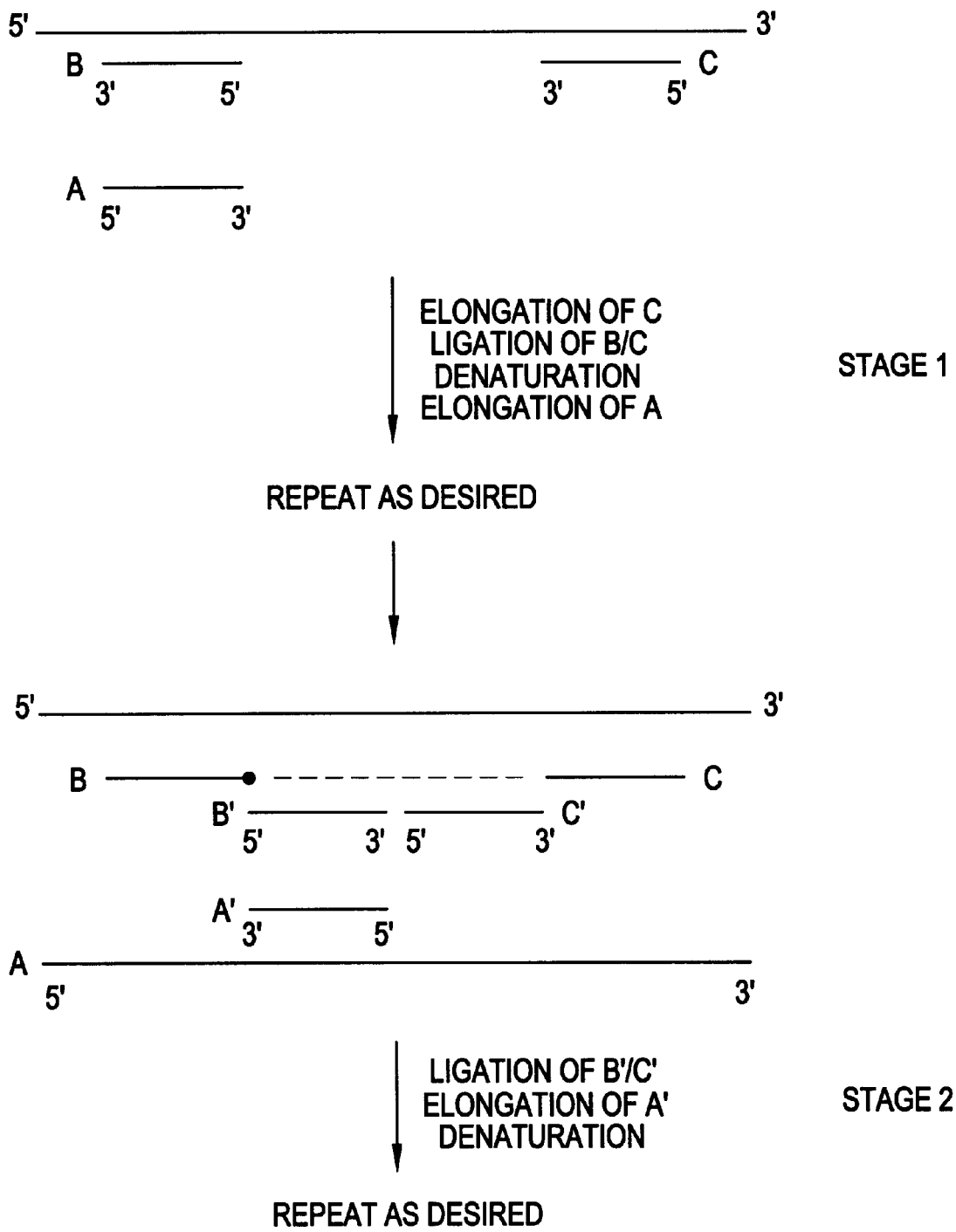
FIG. 8 provides a schematic representation of an alternative embodiment of the invention designated as NERA, where the target is single stranded.

Schematic representations of NERA are set forth in FIG. 2 (double stranded target) of FIG. 8 (single stranded target).

1. Nucleic Acid Target Sequences

The information set forth in Section A.1 is applicable to this embodiment of the invention. As noted, while a "gap" is utilized for NERA, the sequence within the gap must be of sufficient definition such that nested Blocker, Primer and End-Run moieties can be generated which can hybridize to the filled-in portion of the amplified product of the first stage.

2. Blocker/Primer/End-Run

The information set forth in Section B.2 is applicable for the Blocker, Primer and End-Run moieties utilized for the first stage. Because a preferred objective of the first stage is to generate sufficient target for the second stage, labelling is not required in the first stage—as is apparent, detection or capture is not per se necessary under these parameters. Labelling is preferred, however, for the second stage. The information set forth in Sections A.2 is applicable for the nested Blocker, Primer and End-Run moieties utilized in the second stage.

3. Strand Separation/Denaturation

The information set forth in Section A.3 is applicable to this embodiment of the invention.

4. Procedural Steps

For the first stage, the information set forth in Section B.4 is applicable to this embodiment of the invention; it is noted again that the "gap" utilized for NERA has a sequence which is fully or partially defined. After sufficient cycling in the first stage (i.e. between about 5–80 cycles), the reaction can be stopped, preferably by temperature mediation (i.e. lowering the temperature to about 4° C.).

The amplified product of the first stage need not be separated from unused reactants which may be present in the reaction vessel. This is because to the degree that exponential amplification has occurred, the addition of the nested moieties to the reaction vessel will not compete with such unused reactants—the nested moieties, as defined, are designed to hybridize to regions along the amplified product and thus should not, under stringency conditions, hybridize with the unused reactants. However, the amplified products from the first stage can be separated from the unused reactants by, e.g. column chromatography, bio-specific affinity (biotin-avidin, e.g.), gel purification, etc. The skilled artisan will readily understand and be capable of implementing such separation techniques.

For the second stage, the information set forth in Section A.4 is applicable.

5. Oligonucleotide Labelling

As noted, the moieties (and/or dNTPs) from the first stage need not be labelled; amplification of the target, as opposed to detection and/or capture thereof, is the principle objective of the first stage. For the second stage, however, labelling is preferably utilized; thus, the information set forth in Section A.1 is applicable to the components of the second stage.

6. Detection of Amplified Products From Second Stage

The information set forth in Section A.6 is applicable for the detection of the amplified product of the second stage.

D. Loop End-Run Amplification Reaction ("LERA")

As noted, while embodiments of the invention utilize three distinct moieties, Blocker, Primer and End-Run, a unitary Blocker-Primer "hybrid" moiety can also be utilized. Such a modified Blocker-Primer unitary moiety comprises the disclosed features of the Blocker and Primer, the modification involving "tethering" (preferably) the 5' end of the Primer moiety to the 3'-end of the Blocker moiety—the resulting hybrid, then can be described as a generally circular, or "loop", moiety comprising a Blocker and Primer. Embodiments of the ERA protocol which utilize a loop Blocker-Primer hybrid and End-Run moieties are referred to herein as Loop End-Run Amplification ("LERA") reaction.

Tethering of the Blocker to the Primer can be accomplished by any means which will not interfere with hybridization of the Blocker and Primer portions of the Loop to a designated target sequence under stringency conditions, and which will not interfere with exponential amplification of the target sequence. Most preferably, tethering is accomplished by utilization of "non-specific" nucleotides; beneficially, the use of such non-specific nucleotides allows for synthesis of the Loop during preparation of the oligonucleotide moieties, i.e. a single oligonucleotide comprising a Blocker region, a Primer region and a non-specific region (the non-specific region is designed as a sequence not intended to be complementary to any section of the target sequence).

Figure 9A:
FIGS. 9A–D provide a schematic representation of an elongated Loop oligonucleotide moiety comprising a Blocker region and a Primer region.

Referencing FIG. 9A, the Loop can most preferably be synthesized as a single strand; as schematically set forth, Blocker and Primer regions of the Loop are identified, the dashed lines representing the non-specific region (preferably nucleotides). The Blocker and Primer regions are functionally equivalent to the Blocker and Primer moieties of the ERA protocol with a single exception—the blocking group of the Blocker is the non-specific region (i.e. elongation of the 3' end of Blocker, to which the non-specific region is located, cannot occur).

Figure 9B:
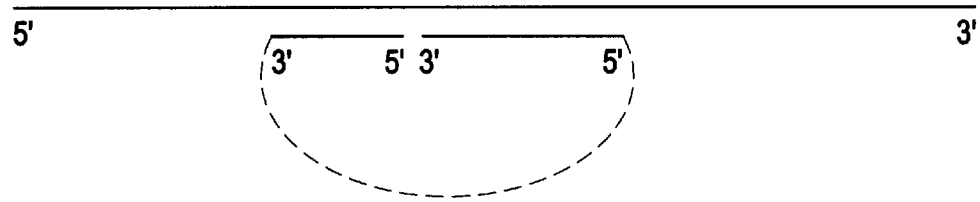

Because the Blocker and Primer regions of the Loop must be capable of hybridizing to the target such that the 5' end of the Blocker region is adjacent to the 3' end of the Primer region (or such that a gap is created between these regions), the non-specific region of the loop must be of sufficient length to allow for hybridization of the Blocker and Primer regions to the target sequence. FIG. 9B schematically represents such hybridization; as can be appreciated, when the Blocker and Primer regions hybridize to the target, a "loop" comprising an opening is formed.

When the non-specific region is comprised of just nucleotides (as is most preferred), the length thereof is preferably greater than about 40 bases, more preferably greater than about 50 bases. When other linkers are utilized, such as, e.g., hydrophilic, linear or branched organic molecules such as a hydrophilic aliphatic linkers, the number of bases can correspondingly decrease. The functional intent of the non-specific region is to provide a sufficient tether that allows for (a) linkage of the Blocker region to the Primer region and (b) hybridization of the Blocker region and Primer region to their respective complementary regions on the target sequences(s). Thus, the skilled artisan will recognize that the non-specific region can comprise a variety of components which can be utilized to accomplish these primary goals.

Figure 9C:
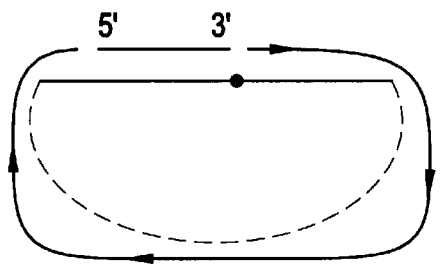

Upon hybridization of the Loop to the target sequence(s), in the case of a single stranded target, a ligation event or a fill-in reaction followed by a ligation event, takes place (if appropriate vis-a-vis the target and the defined sequences of the Blocker and Primer regions of the Loop). This is followed by separation of the completed Loop from the target. The End-Run moiety, which in the LERA embodiment is most preferably complementary to a segment of the Blocker region, is then capable of hybridizing to the completed Loop, and extended along the Loop vis-a-vis, e.g., polymerase and dNTPs. FIG. 9C provides a schematic representation of the hybridization of End-Run to the completed Loop, and elongation of End-Run.

Figure 9D:
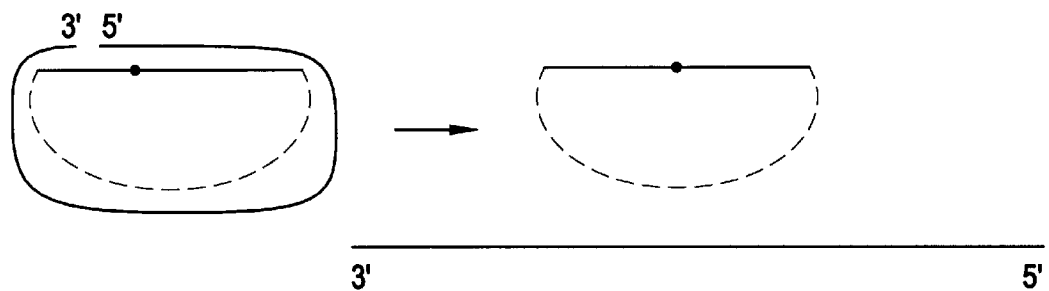
Figure 10:
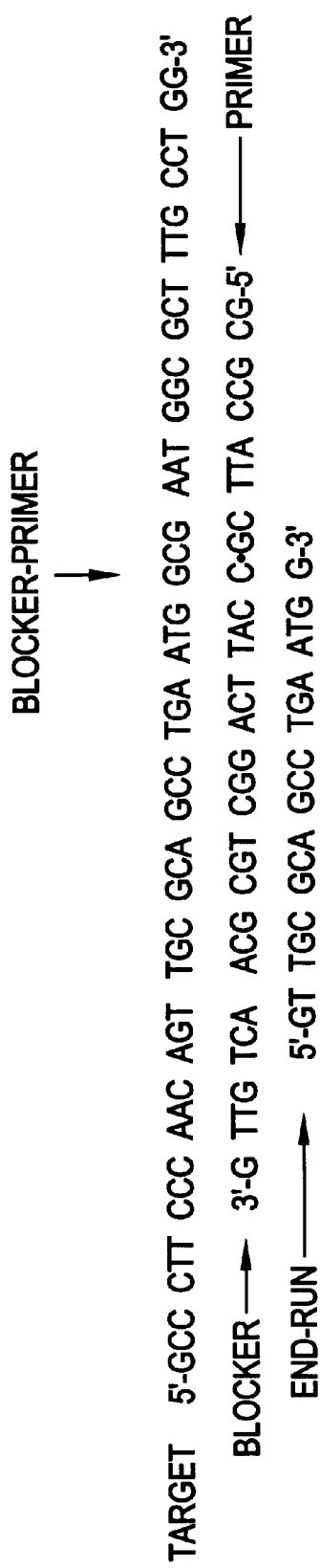
FIG. 10 provides a schematic alignment of the Target, Blocker, Primer and End-Run moieties used for the exponential amplification of the Examples.

As the skilled artisan will appreciate, the presence of, e.g. ligase enzyme within the reaction vessel can catalyze a ligation event between the 5' end of the End-Run moiety, and the 3'-end of the elongated portion thereof. This could lead to the formation of a double stranded covalently closed coiled duplex ("dsCCC"); assuming that a helix turn occurs every ten bases, it may be exceedingly difficult to separate each of the dsCCC strands. This, then, would substantially prevent exponential amplification. Accordingly, it is most preferred that in the LERA embodiment, the 5'-end of the End-Run moiety comprise a blocking group which prevents a ligation event as described in this paragraph from occurring. The blocking group prevents a ligation event such that when the elongated End-Run moiety reaches the 5' end of the End-Run moiety, the elongation ends; under denaturing conditions, then, the elongated End-Run moiety serves as a template comprising regions complementary to the Blocker and Primer regions of the Loop. FIG. 9D schematically represents the separation of extended End-Run from the completed Loop. Accordingly, exponential amplification is viable.

In the case of double stranded target, the LERA is also applicable; additionally, because the End-Run can also hybridize with a section of one of the target strands, elongation of the End-Run moiety along the target strand is also viable.

The non-specific region of the Loop can beneficially comprise regions having functional activity. I.e., the non-specific region is only a moniker vis-a-vis hybridization to the target sequence(s). For example, an alternative approach to the possibility of dcCCC is to incorporate a restriction site(s) within the non-specific region which is amendable to specific cleavage. For example, the Loop moiety may be synthesized such that ribonucleotides are incorporated into the non-specific region; thus, at this section of the Loop, when End-Run elongates therearound, an RNA-DNA hybrid region will be present. Such an RNA-DNA hybrid is amenable to degradation by, e.g., RNAse H such that even with covalent coupling of the End-Run moiety to the elongated portion thereof, such degradation will "open" the enclosed Loop, thus forming the requisite additional template. Beneficially, thermostable RNAse H can be utilized. See, Itaya & Kindo, "Molecular Cloning of Ribonuclease H" *Nuc. Acids Res.* 19/16:4443–4449 (1991), which is incorporated herein by reference.

The non-specific region can also be designed to incorporate a variety of different functional parameters. For example, the non-specific region can incorporate hybridization capture regions for capture of the amplified product, or recognition sequences to which restriction enzymes or DNA binding proteins have a specificity, or primer sets for post-amplification sequencing. Additionally, the non specific regions can incorporate RNA polymerase binding sites such as T7 or SP6 binding sites; these sites allow for transcription (in the presence of, e.g., RNA polymerase and ribonucleotide triphosphates).

Beneficially, a strand that is formed via RNA polymerase mediated elongation is displaced from the Loop without the need for, e.g., heat denaturation. Thus, with the addition of RNA polymerase and ribonucleotide triphosphates, multiple copies of template will be generated from even a single closed Loop. This leads to greater than exponential amplification. E.g., if 10 copies of each closed Loop is generated, then each cycle will generate a theoretical maximum of $10^x$ amplicons, as opposed to $2^x$ amplicons (x being the number of cycles). Furthermore, because the amplified strands mediated by RNA polymerase are displaced without the need for denaturation, the cycling reactions can be run at isothermal temperatures, i.e. about 37° C.; as will be appreciated, this allows for the use of non-thermostable ligase and polymerase, and avoids the need for thermocycling.

A limitation to RNA polymerase mediated LERA as described above is the eventual exhaustion of RNA polymerase enzyme and ribonucleotide triphosphates. Optimization of the RNA polymerase, ligase and DNA polymerase ratios is within the purview of the skilled artisan. It is preferred that the ratio of RNA polymerase to ligase and/or DNA polymerase be at least about 5:1:1 or greater. Additionally, the ratio of total ribonucleotide triphosphates to total deoxyribonucleotide triphosphates is preferably at least about 5:1 or greater.

Because the LERA embodiment is functionally equivalent to the ERA protocol, the foregoing subsections for Adjacent Blocker-Primer and GAP Blocker-Primer are applicable to LERA.

EXAMPLES

The following examples directed to preferred embodiments of the invention disclosed herein are not intended, nor should they be construed, as limiting the disclosure, or the claims to follow.

I. MATERALS AND METHODS

Example I

A. Oligonucleotide Moiety and Target Synthesis

Synthesis of oligonucleotide moieties (Blocker, Primer, End-Run) and a single stranded Target was performed on a Pharmacia LKB (Upsalla, Sweden) Gene Assembler® plus DNA synthesizer using Beckman Instruments, Inc. (Fullerton, Calif.) phosphoramidites (Product Nos. A:338231; C:338232; G:338233; T:338234). Manufacturer instructions were followed for synthesis, deprotection and cleavage.

Sequences generated were as follows:
Target (SEO ID NO.8)
    5'-GCC CTT CCC AAC AGT TGC GCA GCC TGA ATG GCG AAT GGC GCT TTG CCT GG-3' 50-mer
Blocker (SEQ ID NO.9)
    5'-CCA TTC AGG CTG CGC AAC TGT TG-3' 23-mer
Primer (SEQ ID NO.10)
    5'-GCG CCA TTC G-3' 10-mer
End-Run (SEQ ID NO.11)
    5'-GTT GCG CAG CCT GAA TGG -3' 18-mer
A ddGTP was added to the 3' terminus of the Blocker moiety; thus the Blocker moiety was a 24-mer during the ERA reaction.

Figure 11:
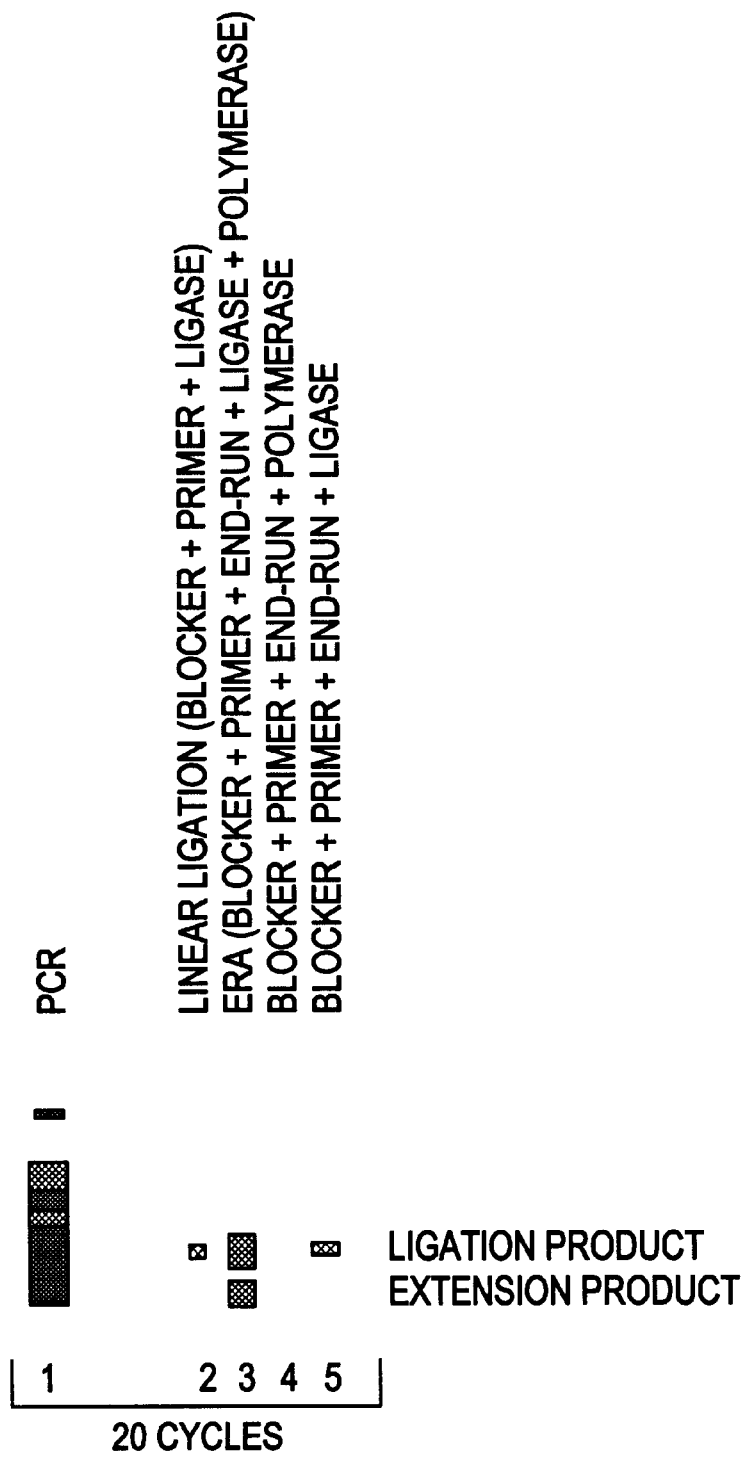
FIG. 11 provides the results of, inter alia, the exponential amplification of the Target of FIG. 10 using the Blocker, Primer and End-Run moieties in accordance with the disclosed amplification procedure.

A schematic alignment of the blocker, Primer and End-Run oligonucleotide moieties, vis-a-vis the Target, is presented in FIG. 11. The break or "nick" in the nucleic acid sequence shown at the 3' terminus of the primer and the 5' terminus of the blocker is represented by "•".

B. Thermal Cycler

A Perkin Elmer Thermal Cycler 480™ was utilized. Manufacturer instructions were followed.

C. Ligase and Polymerase Enzymes

Ligase enzyme was AMPLIGASE™ thermostable DNA ligase (Epicentre Technologies, Madison, Wis. CAT. NO. A00101, 5000 units; as defined "one unit catalyzes ligation of 50% of the cos sites in one microgram of bacteriophage lambda DNA in 1 minute at 45° C. in standard 50 µl reaction.") The enzyme has a stated half-life of 48 hrs. at 65° C., and 1 hr. at 95° C.

Polymerase enzyme was AmpliTaq® DNA polymerase (Perkin Elmer, Norwalk, Conn., Cat. No. N801-0060).

D. Deoxynucleoside Triphosphates dNTPs were obtained from a GeneAmp® PCR Reagent Kit (Perkin Elmer, Cat. No. N801-0055).

E. Reaction Buffer

All chemicals were at least of ACS grade. Concentrations of compounds in a 10× reaction buffer concentrate in a final volume of 1.0 ml (adjusted with double distilled water) were as follows: 100 mM tris hydroxymethyl amino methane hydrochloric acid ("Tris-HCL"), pH 7.8; 500 mM potassium chloride; 150 mM magnesium chloride; 25 mM NAD$^+$; and 0.01% (w/v) gelatin (Sigma, St. Louis, Mo., Cat. No. G2500).

F. Moiety Labelling

The Primer and End-Run oligonucleotide moieties were labelled using T4 polynucleotide kinase and $\gamma^{32}$P ATP (Amersham) following the protocol described in Maniatis (1989, pp. 11.31–11.32). The reaction condition was modified whereby the labelling reaction was conducted at 37° C. for 1 hr., followed by the addition of 0.5M "cold" ATP (i.e. non-radioactive) to ensure that all kinased ends that did not incorporate radioactive PO$_4$ incorporated the cold PO$_4$. The Blocker comprised a "cold" 5'-PO$_4$ terminus.

G. End-Run Amplification Reaction Protocol

The various components were initially admixed in a reaction vessel on ice (4° C.) in order to prevent hybridization and enzymatic activity.

Initially, 5 µl of the 10× reaction buffer was added to a 500 µl vessel, followed by 1 µl target sequence (this provided a 50 nM final concentration in 20 µl total solution). Thereafter, each of the four dNTPs were added to achieve a final concentration of 200 µM for each of dATP, dTTP, dCTP, and dGTP in 20 µl total solution. To this admixture was added the labelled oligonucleotide moieties such that a final concentration of 200 nM Blocker, 200 nM Primer and 150 nM End-Run in 20 µl total solution was achieved. This was followed by the addition of 1 unit of the aforementioned ligase enzyme, followed by the addition of 1 unit of the aforementioned polymerase enzyme. Sufficient double deionized water was then added to achieve a final volume of 20 µl.

After the components were admixed, the reaction vessel was heated to 95° C. for 5 min. on the aforementioned thermal cycler. This was followed by 20 cycles, each cycle having the following parameters: 95° C.—1 min.; 75° C.—4 min.; 45° C.—4 min. After the final cycle, the reaction vessel was then maintained at 4° C. until analysis.

H. Polymerase Chain Reaction Protocol (PCR Control)

The ERA protocol of Section I.F. was modified in order to obtain a PCR comparative control, the exception being that the Blocker oligonucleotide moiety was not utilized.

I. Linear Ligation Protocol (Oligonucleotide Ligation Assay Control)

The ERA protocol of Section I.F. was modified in order to obtain a linear ligation comparative control, the exception being that the End-Run oligonucleotide moiety was not utilized.

J. Negative Control—Non-Ligase Enzyme Condition

The ERA protocol of Section I.F. was modified in order to obtain an incomplete ERA reaction, the exception being that the ligase enzyme was not utilized.

K. Negative Control—Non-Polymerase Enzyme Condition

The ERA protocol of Section I.F. was modified in order to obtain an incomplete ERA reaction, the exception being that the polymerase enzyme was not utilized.

L. Analysis

After the 20 cycles, 3 µl urea "stop" dye (50% urea, 1% xylene cyanol, 1% bromophenol blue, 0.2×TBE) was added to separate 10 µl aliquots obtained from each of the reaction vessels of Sections I.F–J. Thereafter, the reaction vessels was boiled for 10 min. followed by loading onto an electrophoresis slab gel (15% acrylamide gel, 19:1 acrylamide:bis-acrylamide in 7M urea and 1×TBE). Electrophoresis was conducted using 250 volts (50 mA) for 2 hrs. Thereafter, the electrophoresed aliquots were exposed to Kodak X-OMAT™ AR x-ray film (Eastman Kodak, Rochester, N.Y. Cat. No. 165-1512) for 90 min.

Example II

A. Oligonucleotide Moiety and Target Synthesis

For Example II, the synthesis and sequences for Target, Primer and End-Run were as in Example I. Blocker was synthesized using a Biosearch 8750™ oligonucleotide synthesizer (Milligen Biosearch, Sam Rafael, Calif.) to generate a Blocker as defined in Example I comprising a biotin molecule at the 3'-end thereof; a 3'-Biotin-ON CPG column (Clonetecn Labs, Inc., Palo Alto, Calif. Cat. No. 5225-1) was utilized for Blocker synthesis.

B. Thermal Cycler

The same thermal cycler of Example I was utilized.

C. Ligase and Polymerase

Ligase enzyme was as in Example I. Polymerase enzyme was Amplitaq® DNA polymerase, Stoffel Fragment (exonuclease deficient version) (Perkin Elmer Cat. No. N808-0038).

D. Deoxynucleoside Triphosphates dNTPs were as in Example I.

E. Reaction Buffer

All chemicals were at least of ACS grade. Concentrations of the components in a 10× reaction buffer concentrate in a final volume of 1.0 ml (adjusted with double distilled water) were as follows: 200 mM TRIS-HCl, pH 7.8; 200 mM potassium chloride; 25 mM ammonium chloride; 20 mM magnesium chloride; 50 mM dithiothretiol; 500 µM NAD$^+$; 500µg/ml bovine serum albumin; and 1% Triton X-100™ (Sigma, Cat. No. T6878).

F. Moiety Labelling

In Example II, End-Run and Primer were labelled as in Example I, and Blocker was labelled as set forth for End-Run and Primer in Example I (i.e. Blocker comprised a radioactive label).

G. Rnd-Run Amplification Reaction Protocol

The various components were initially admixed in a reaction vessel on ice (4° C.) in order to substantially prevent hybridization and non-specific hybridization.

Initially, 5 µl of the 10× reaction buffer was added to a 500 µl vessel, followed by addition of 1 µl of a 1.0 nM stock solution of target sequence (final target sequence concentration in 50 µl total solution: 20 picomolar) or 1 µl of a 1.0 pM stock solution of target sequence (final target sequence concentration in 50 µl total solution: 20 femtomolar. Thereafter, each of the four dNTPs were added to achieve a final concentration of 200 µM for each of dATP, dTTP, dCTP and dGTP in 50 µl total solution. To this admixture was added the labelled oligonucleotide moieties such that a final concentration of 120 nM Blocker, 40 nM Primer and 40 nM End-Run (3:1:1 of Blocker:Primer:End-Run) in 50 µl total solution was achieved. This was followed by the addition of 10 units of the aforementioned ligase enzyme, followed by sufficient double deionized water to achieve a volume of 49 µl.

After the components were admixed, the reaction vessel was heated to 95° C. for 5 min. on the aforementioned thermal cycler to achieve complete denaturation of target and oligonucleotide moieties. this was followed by the addition of 2 units (1 µl) of the aforementioned polymerase enzyme to the reaction vessel. This was followed by 40 cycles, each cycle having the following parameters: 95° C.—1 min.; 70° C.—4 min.; 40° C.—4 min. After the final cycle, the reaction vessel was then maintained at 4° C. until analysis.

H. Polymerase Chain Reaction Protocol PCR Control)

The ERA protocol of Example II.G was modified in order to obtain a PCR comparative control, the exception being the Blocker oligonucleotide was not utilized in the reaction mixture.

I. Negative Control—Non Ligase Enzyme Condition

The ERA protocol of Example II.G was modified in order to obtain an incomplete ERA reaction, the exception being that the ligase enzyme was not utilized.

J. Negative Control—Non-Polymerase Enzyme Condition

The ERA protocol of Example II.G was modified in order to obtain an incomplete ERA reaction, the exception being that the polymerase enzyme was not utilized.

K. Analysis

After 40 cycles, 3 µl "stop" dye (as described in Example I.L.) was added to separate 10 µl aliquots obtained from each of the reaction vessels of Sections II.G–I. Thereafter, the aliquots were boiled for 10 min. followed by loading into an electrophoresis slab gel (as described in Example I.L). Electrophoresis was conducted and exposure was obtained as in Example I.L.

II. RESULTS

A. Example I

FIG. 11 provides a photographic reproduction of the results of the electrophoresis of the aliquots obtained from the reaction vessels of Example I. F–J. In FIG. 11, lane 1 provides the results of a PCR amplification of the target sequence; lane 2 provides the results of the linear ligation amplification of the target sequence; lane 3 provides the results of End-Run Amplification of the target sequence; lane 4 provides an incomplete ERA reaction (-ligase); and lane 5 provides an incomplete ERA reaction (-polymerase). Amplification of the target sequence using a PCR protocol is evident from the results of lane 1 of FIG. 11; because all of the conditions were substantially identical for each protocol (except, of course, when differences were utilized as described above), the results of lane 1 indicate that the parameters utilized did not interfere with PCR amplification of the target sequence.

FIG. 11 provides information regarding several aspects of the disclosed ERA protocol. As is evident from the exposed dark bands of lane 3, amplification of the target sequence was accomplished using the ERA protocol; two bands are found in lane 3, one resulting from amplification of a so-called "extension product" and one from amplification of a so-called "ligation product". Referencing FIG. 11, because the End-Run moiety is "shorter" than the Blocker, extension of the End-Run moieties will result in amplified products which are "shorter" than amplified products resulting from the ligation of the Blocker and Primer.

As would be expected, in the condition where ligase enzyme was not utilized (lane 4) whereby the Blocker and Primer would be unable to be covalently bound to one another, no amplification of the target sequence occurred. This is because without the ligation event (and, in these examples, because of the use of a single-stranded target), there is an unavailability of ligation product target sequences, but such that of End-Run can only hybridize with the Blocker.

Lanes 2 and 5 evidence that the ERA protocol does not result in exponential amplification unless all of the moieties are utilized. Lane 2, which provided an OLA control, evidences linear amplification of the target sequence (based upon, e.g., the relative size and density of the autoradiograph band), as would be expected. OLA does not result in exponential amplification, in that only two "primers" and a ligase enzyme are utilized. However, even when the End-Run moiety is added in the absence of polymerase to the reaction vessel (lane 5), the resulting band is essentially identical to that of lane 2.

The results evidence that the ERA protocol disclosed herein is a unique and viable approach to amplification of a target sequence.

Example II

Example II differs from Example I principally in terms of target concentration. In Example I, the target concentration was about $10^{-9}$ molar (i.e. $10^{12}$ molecules). In Example II, the target concentration was about $10^{-12}$ molar (i.e. $10^9$ molecules) (FIG. 12A) and $10^{-15}$ molar ($10^6$ molecules) (FIG. 12B)—this concentration is within the range necessary for detection of a single gene within a human sample.

Figure 12:
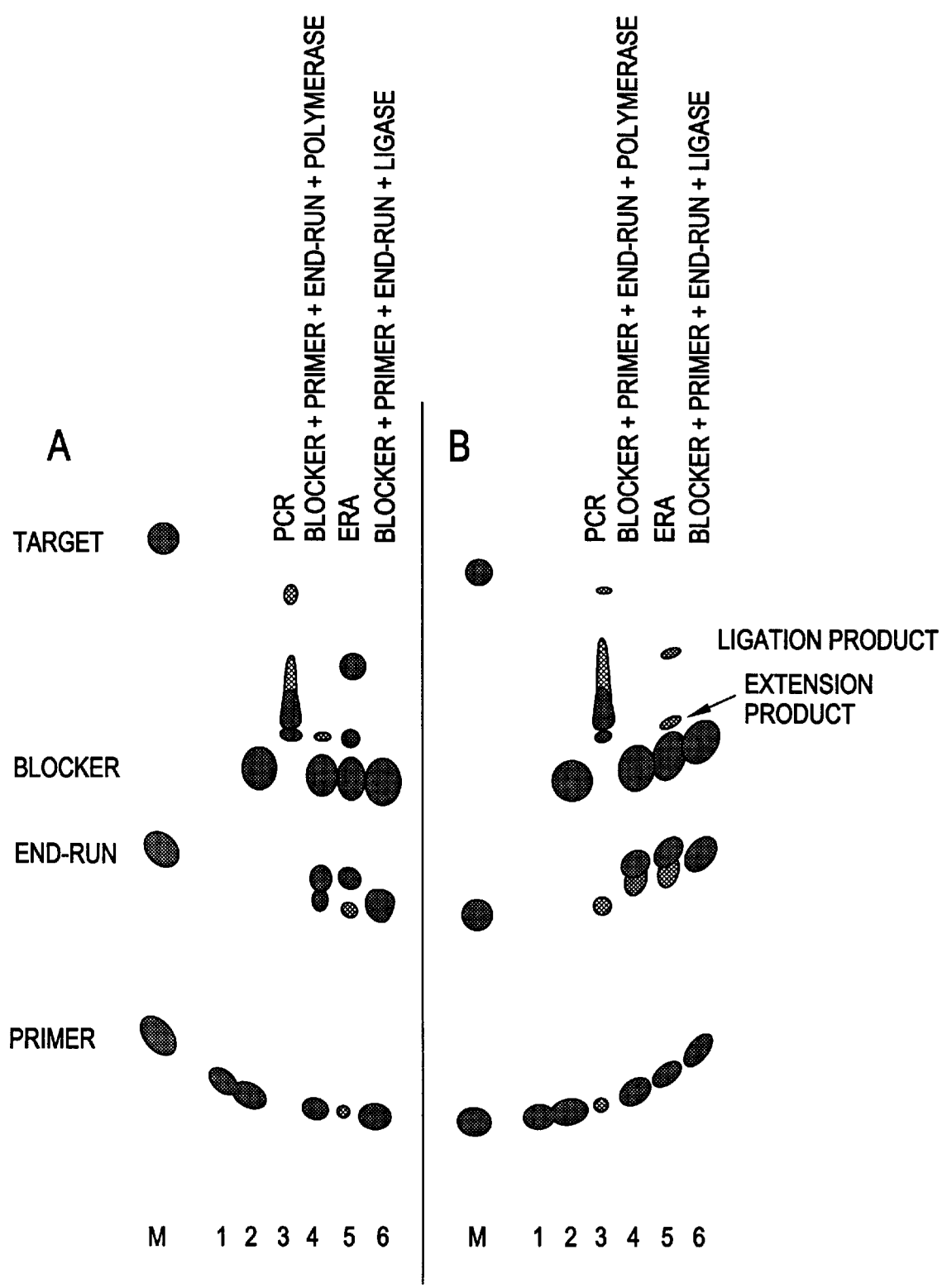
FIG. 12 provides the results of, inter alia, the exponential amplification of the target of FIG. 10 using the moieties described in FIG. 11.

FIG. 12 provides a photographic reproduction of the results of the electrophoresis of the aliquots obtained from the reaction vessels of Example II G–I. In FIG. 12A, lane M provides the exposure resulting from End-Run, Primer Target (Blocker is present in lane 2); lane 3 provides the results of a PCR amplification of the target sequence; lane 4 demonstrates the results of an incomplete ERA reaction (-ligase); lane 5 provides the results of End-Run Amplification of the target sequence; and lane 6 provides the results of an incomplete ERA reaction (-polymerase). The designations are the same for FIG. 12B. As with Example I, amplification of the target sequence using a PCR protocol is evident from the results of lane 3 of FIGS. 12A and B; again, because all of the conditions were substantially identical for each protocol, the results of lane 3 indicate that the parameters utilized did not interfere with PCR amplification of the target sequence.

FIG. 12 also provides information regarding several aspects of the disclosed ERA protocol as set forth above. Most importantly, FIG. 12B evidences that detection and amplification of a target sequence present at a concentration similar to that for a gene of interest can be accomplished using the disclosed ERA protocol.

Modifications of the disclosed ERA protocol, which result in substantially equivalent results, will be readily apparent to those in the art. For example, and not limitation, an "inverse ERA" reaction, such as that described in U.S. Pat. No. 4,994,370 vis-a-vis PCR, is viable. Additionally, it is possible to utilize, e.g., a Blocker moiety that "overhangs" the point of ligation with the Primer such that the, e.g., Blocker, is amenable to a "chew-back" reaction. See, for example, Holland et al *PNAS* 88:7276–7280 (1991). Other modifications will be readily apparent to those in the art and these are considered to fall within the scope of the following claims.

What is claimed is:

1. A kit comprising reagents for amplification of at least one target sequence comprising at least one region having a defined nucleic acid sequence, the kit comprising at least one Blocker moiety, at least one Primer moiety, and at least one End-Run moiety, where the Blocker moiety is capable of hybridizing to the nucleic acid sequence, the Primer moiety is capable of hybridizing to the nucleic acid sequence such that the Primer moiety abuts the hybridized Blocker moiety or is capable of extending to the hybridized Blocker moiety, and the End-Run moiety comprises a sequence which is complementary to at least a portion of the Blocker moiety.

2. The kit of claim 1 further including at least one buffer capable of providing a pH of between 6 and 9 for said amplification.

3. The kit of claim 1 further including additives selected from the group consisting of potassium chloride, magnesium chloride, dithiothreitol, nicotinamide adenine dinucleotide, bovine serum albumin, nonionic detergent, and nucleotide triphosphates.

4. The kit of claim 1 further including at least one enzyme selected from the group consisting of polymerase and ligase.

5. A kit comprising components for conducting a reaction for amplifying or detecting a target sequence of a polynucleotide, said reaction comprising the steps:

a) treating said polynucleotide with at least three oligonucleotide moieties wherein said at least three oligonucleotide moieties include:

i) a first oligonucleotide moiety comprising a nucleotide sequence complementary to and capable of hybridizing to the polynucleotide;

ii) a second oligonucleotide moiety complementary to and capable of hybridizing to the polynucleotide such that the second oligonucleotide moiety abuts the first oligonucleotide moiety when the first oligonucleotide moiety is hybridized to the polynucleotide or such that the second oligonucleotide is capable of extending to the first oligonucleotide moiety when the first oligonucleotide moiety is hybridized to the polynucleotide; and iii) a third oligonucleotide moiety comprising a sequence which is complementary to at least a portion of the first oligonucleotide moiety;

b) providing conditions for hybridizing the first moiety and the second moiety to the polynucleotide;

c) providing conditions for ligating the hybridized first moiety to the hybridized second moiety to form a ligation product; and d) providing conditions for hybridizing and chain extending the third moiety, said components being capable of buffering said reaction to a pH of 6–9 and capable of promoting ligase and polymerase specificity and processivity.

6. The kit of claim 5 wherein the buffering compound is tris hydroxymethyl amino methane hydrochloric acid.

7. The kit of claim 5 further including additives selected from the group consisting of potassium chloride, magnesium chloride, dithiothreitol, nicotinamide adenine dinucleotide, bovine serum albumin, and nonionic detergent.

* * * * *